(12) United States Patent
Lee et al.

(10) Patent No.: US 12,303,157 B2
(45) Date of Patent: *May 20, 2025

(54) SURGICAL INSTRUMENT

(71) Applicant: LIVSMED INC., Seongnam-si (KR)

(72) Inventors: Jung Joo Lee, Seongnam-si (KR);
Heejin Kim, Seongnam-si (KR);
Dongkyu Jang, Seongnam-si (KR)

(73) Assignee: LIVSMED INC., Seongnam-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/663,924

(22) Filed: May 14, 2024

(65) Prior Publication Data

US 2024/0299058 A1    Sep. 12, 2024

Related U.S. Application Data

(63) Continuation of application No. 17/991,831, filed on Nov. 21, 2022, now Pat. No. 12,016,586, which is a continuation of application No. 17/543,392, filed on Dec. 6, 2021, now Pat. No. 11,504,145.

(30) Foreign Application Priority Data

Jan. 8, 2021    (KR) .......................... 10-2021-0002792

(51) Int. Cl.
*A61B 17/29*    (2006.01)
(52) U.S. Cl.
CPC .. *A61B 17/2909* (2013.01); *A61B 2017/2933* (2013.01); *A61B 2017/2946* (2013.01); *A61B 2017/2947* (2013.01)

(58) Field of Classification Search
CPC ........ A61B 17/2909; A61B 2017/2925; A61B 2017/2912; A61B 2017/2919; A61B 2017/291; A61B 2017/2923; A61B 2017/292; A61B 2017/2913; A61B 2017/2946; A61B 34/71; A61B 34/30; A61B 34/70; A61B 2034/305
See application file for complete search history.

(56) References Cited

U.S. PATENT DOCUMENTS

2007/0208375 A1    9/2007  Nishizawa et al.
2013/0140835 A1*   6/2013  Stefanchik ............. A61B 17/29
                                                              294/106

FOREIGN PATENT DOCUMENTS

| JP | 2001-046384 A | 2/2001 |
| JP | 2004-130074 A | 4/2004 |
| JP | 2010-220786 A | 10/2010 |
| JP | 2013-541996 A | 11/2013 |
| JP | 2015-128616 A | 7/2015 |
| JP | 2018-514268 A | 6/2018 |
| KR | 10-2118721 B1 | 6/2020 |
| KR | 10-2122508 B1 | 6/2020 |

* cited by examiner

*Primary Examiner* — Majid Jamialahmadi
(74) *Attorney, Agent, or Firm* — Bridgeway IP Law Group, PLLC; Sang Ho Lee; Hyun Woo Shin

(57) ABSTRACT

Surgical instrument is provided. The surgical instrument is capable of being operated manually or automatically for use in laparoscopic surgery or various surgeries and includes a locking device capable of locking and/or unlocking at least one operation.

14 Claims, 19 Drawing Sheets

SURGICAL INSTRUMENT

CROSS-REFERENCE TO RELATED APPLICATION

The present application is a continuation application of U.S. application Ser. No. 17/991,831 filed on Nov. 21, 2022, which is a continuation application of U.S. application Ser. No. 17/543,392 filed on Dec. 6, 2021 (issued as U.S. Pat. No. 11,504,145 on Nov. 22, 2022), and claims priority under 35 U.S.C. § 119 to Korean patent application No. 10-2021-0002792 filed on Jan. 8, 2021, the entire disclosures of which are hereby incorporated by reference.

BACKGROUND

1. Field

One or more embodiments relate to surgical instrument, and more particularly, to surgical instrument capable of being operated manually or automatically for use in laparoscopic surgery or various surgeries and including a locking device capable of locking and/or unlocking at least one operation.

2. Description of the Related Art

Medically, surgery refers to the treatment of diseases by cutting, slitting, or manipulating the skin, mucous membranes, or other tissues using medical devices. In particular, open surgery in which the skin of the surgical site is incised and opened to treat, shape, or remove organs, etc. therein and the like cause problems such as bleeding, side effects, patient pain, scarring. Therefore, recently, surgery performed by inserting only a medical device, for example, laparoscopic surgical instrument, microsurgical microscope, etc., by forming a predetermined hole in the skin or surgery using a robot has been spotlighted as an alternative.

The surgical instrument is a tool for operating on a surgical site by a doctor manipulating an end tool provided at one end of a shaft passing through a hole drilled in the skin with a predetermined driving portion or a robot arm. The end tool provided in the surgical instrument performs rotational operation, gripping operation, cutting operation, etc. through a predetermined structure.

However, there was a need for the surgical instrument to be maintained in a specific position even if a user does not apply force to the surgical instrument while performing surgery using such a surgical instrument, that is, a need for a lock state. For example, there was a need for a first surgical instrument to be locked while holding a patient's tissue when a doctor intends to suture the tissue held by the first surgical instrument using a second surgical instrument while the first surgical instrument is holding the tissue.

The above-mentioned background art is technical information that the inventor has possessed for the derivation of the present disclosure or acquired in the process of derivation of the present disclosure, and cannot necessarily be said to be a known technique disclosed to the general public prior to the filing of the present disclosure.

SUMMARY

One or more embodiments include a surgical instrument capable of being operated manually or automatically for use in laparoscopic surgery or various surgeries and comprising a locking device capable of locking and/or unlocking at least one operation.

Additional aspects will be set forth in part in the description which follows and, in part, will be apparent from the description, or may be learned by practice of the presented embodiments of the disclosure.

According to one or more embodiments, surgical instrument includes: an end tool having a first jaw and a second jaw, each formed to be rotatable, wherein the rotation is made in two or more directions; a manipulation portion configured to control rotation of the end tool in the two or more directions; a power transmission portion having a first jaw wire connected to the manipulation portion to transfer the rotation of the manipulation portion to the first jaw and a second jaw wire connected to the manipulation portion to transfer the rotation of the manipulation portion to the second jaw; and a connecting portion extending in a first direction (X-axis) and having one end coupled to the end tool and the other end coupled to the manipulation portion to connect the manipulation portion and the end tool, wherein the manipulation portion includes an actuation manipulation portion configured to control actuation movement of the end tool, and a locking device formed to be able to be in contact with the actuation manipulation portion and locking or unlocking actuation operation of the actuation manipulation portion depending on whether the locking device is in contact with the actuation manipulation portion.

In an embodiment, a first coupling portion may be formed in the actuation manipulation portion, and a locking portion formed to be able to be in contact with the first coupling portion may be formed in the locking device.

In an embodiment, the locking portion may be formed to engage the first coupling portion when the locking portion is in a first position to restrict movement of the first coupling portion, and the locking portion may be formed to be spaced apart from the first coupling portion to a certain extent when the locking portion is in a second position to enable movement of the first coupling portion.

In an embodiment, the surgical instrument may further include a locking control portion configured to control a position of the locking portion so that the locking portion maintains either the first position or the second position.

In an embodiment, the locking control portion may include a body portion disposed within the manipulation portion, and a pressing portion coupled to the body portion and formed to be able to be drawn in and drawn out from the body portion.

In an embodiment, the pressing portion may be drawn in the body portion when the pressing portion is pressed once, and the pressing portion may be drawn out from the body portion when the pressing portion is pressed once again.

In an embodiment, the locking portion may be positioned in the second position while the pressing portion is drawn in the body portion when the pressing portion is pressed once, and the locking portion may be positioned at the first position while the pressing portion is drawn out from the body portion when the pressing portion is pressed once again.

In an embodiment, a plunger is disposed on any one of the body portion and the pressing portion, and a cam body is disposed on the other one of the body portion and the pressing portion, so that the position of the pressing portion with respect to the body portion may be controlled by the relative positional relationship between the plunger and the cam body.

In an embodiment, the surgical instrument may further include a second elastic member providing a predetermined elastic force to at least one of the plunger and the cam body.

In an embodiment, a first elastic member is arranged between the locking portion and an inner wall of a first handle to apply a predetermined elastic force to the locking portion so that the locking portion may be positioned in the second position.

In an embodiment, the locking device may be capable of locking the actuation manipulation portion in one or more locking positions.

In an embodiment, the first coupling portion may be formed in a gear-shape having one or more cog wheels, and each cog wheel mat correspond to the corresponding locking position.

In an embodiment, one surface of the locking portion and one surface of the first coupling portion are each formed to be inclined at a predetermined angle, so that may function as a ratchet when the locking portion and the first coupling portion are fastened to each other.

In an embodiment, the first coupling portion may be formed to be rotatable in only one of a clockwise direction and a counterclockwise direction while the locking portion and the first coupling portion are fastened to each other.

In an embodiment, the manipulation portion further includes a first handle, a yaw manipulation portion formed to be connected to the first handle and controls a yaw movement of the end tool, and a pitch manipulation portion formed on one side of the yaw manipulation portion and controlling a pitch movement of the end tool, and the actuation manipulation portion may be formed on the other side of the yaw manipulation portion.

According to one or more embodiments, surgical Instrument includes an end tool having a first jaw and a second jaw, each formed to be rotatable, wherein the rotation is made in two or more directions; a manipulation portion configured to control rotation of the end tool in the two or more directions; a power transmission portion having a first jaw wire connected to the manipulation portion to transfer the rotation of the manipulation portion to the first jaw and a second jaw wire connected to the manipulation portion to transfer the rotation of the manipulation portion to the second jaw; and a connecting portion extending in a first direction (X-axis) and having one end coupled to the end tool and the other end coupled to the manipulation portion to connect the manipulation portion and the end tool, wherein the manipulation portion includes an actuation manipulation portion having a first coupling portion and controlling an actuation movement of the end tool, and a locking device including a locking portion having a second coupling portion formed to be able to be coupled to the first coupling portion and locking or unlocking the actuation operation of the actuation manipulation portion depending on whether the first coupling portion and the second coupling portion are coupled to each other.

According to one or more embodiments, the first coupling portion and the second coupling portion may be formed to be able to be coupled to each other when the locking portion is in a first position, and the first coupling portion and the second coupling portion may be formed to be spaced apart from each other by a certain degree when the locking portion is in a second position.

According to one or more embodiments, movement of the actuation manipulation portion may be restricted when the locking portion is in the first position, and the actuation manipulation portion is allowed to move when the locking portion is in the second position.

According to one or more embodiments, the first coupling portion may be formed as a gear-shape having one or more cog wheels, and each cog wheel may correspond to the corresponding locking position.

According to one or more embodiments, the second coupling portion is formed in a hook-shape, and may be formed to be engageable with each cog wheel of the first coupling portion.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1A:
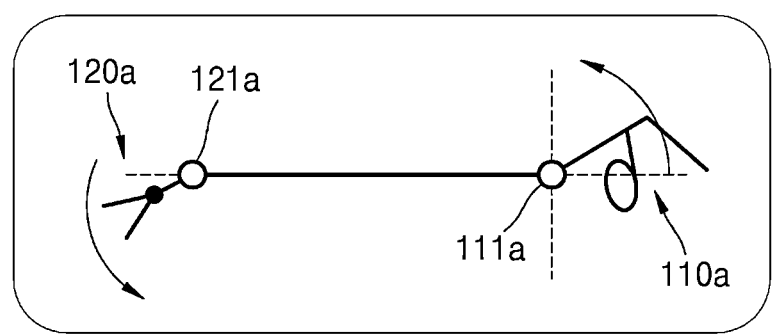
FIG. 1A is a conceptual diagram of a pitch operation of a conventional surgical instrument.

The present disclosure may include various embodiments and modifications, and particular embodiments thereof are illustrated in the drawings and will be described herein in detail. However, it will be understood that the present disclosure is not limited to the embodiments and includes all modifications, equivalents, and replacements within the idea and technical scope of the present disclosure. Moreover, detailed descriptions related to well-known functions or configurations will be omitted in order not to unnecessarily obscure subject matters of the present disclosure.

Although terms such as "first" and "second" may be used herein to describe various elements or components, these elements or components should not be limited by these terms. These terms are only used to distinguish one element or component from other elements or components.

The terminology used herein is for explaining specific embodiments only and is not intended to limit the present disclosure. As used herein, the singular forms "a," "an", and "the" are intended to include the plural forms as well, unless the context clearly indicates otherwise. It will be understood that terms such as "comprise," "include," and "have," when used herein, specify the presence of state features, integers, steps, operations, elements, components, or combinations thereof, but do not preclude the presence or addition of one or more other features, integers, steps, operations, elements, components, or combinations thereof.

Hereinafter, embodiments of the present disclosure will be described in detail with reference to the accompanying drawings. In the following description, like reference numerals denote like elements, and redundant descriptions thereof will be omitted.

In addition, it will be understood that various embodiments of the present disclosure may be interpreted or implemented in combination, and technical features of each embodiment may be interpreted or implemented in combination with technical features of other embodiments.

An instrument for surgery of the present disclosure is characterized in that if a manipulation part is rotated in one direction for at least any one of pitch, yaw, and actuation motions, an end tool is rotated in intuitively the same direction as the direction in which the manipulation part is manipulated.

Figure 1B:
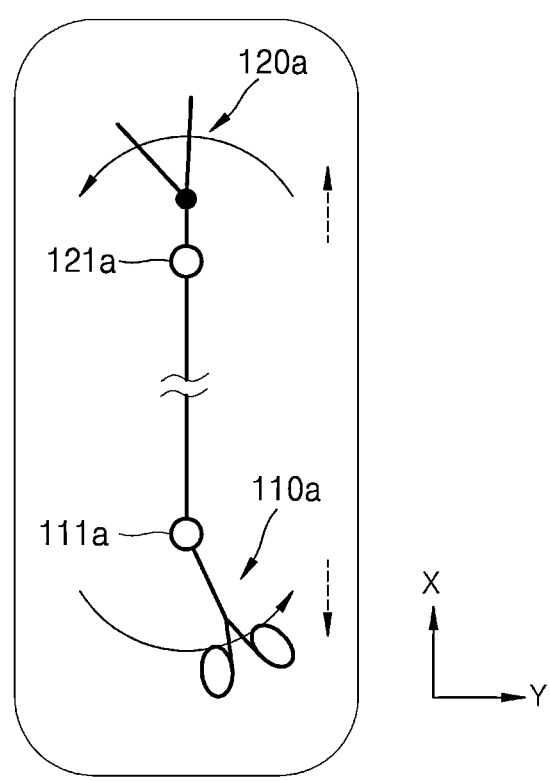
FIG. 1B is a conceptual diagram of a yaw operation.

FIG. 1A is a schematic view illustrating pitch motion of an instrument for surgery of the related art, and FIG. 1B is a schematic view illustrating yaw motion of the instrument for surgery of the related art.

Referring to FIG. 1A, a pitch motion of the instrument for surgery of the related art is performed as follows. In a state in which an end tool 120a is in front of an end tool rotation center 121a and a manipulation part 110a is in back of a manipulation part rotation center 111a, if the manipulation part 110a is rotated clockwise, the end tool 120a is also rotated clockwise, and if the manipulation part 110a is rotated counterclockwise, the end tool 120a is also rotated counterclockwise. Referring to FIG. 1B, a yaw motion of the instrument for surgery of the related art is performed as follows. In a state in which the end tool 120a is in front of the end tool rotation center 121a and the manipulation part 110a is in back of the manipulation part rotation center 111a, if the manipulation part 110a is rotated clockwise, the end tool 120a is also rotated clockwise, and if the manipulation part 110a is rotated counterclockwise, the end tool 120a is also rotated counterclockwise. In this case, from the viewpoint of a horizontal direction of a user, when the user moves the manipulation part 110a to the left, the end tool 120a moves to the right, and when the user moves the manipulation part 110a to the right, the end tool 120a moves to the left. Consequently, since the manipulation direction of the user and the operation direction of the end tool are opposite each other, the user may make mistakes and have difficulty in manipulation.

Figure 1C:
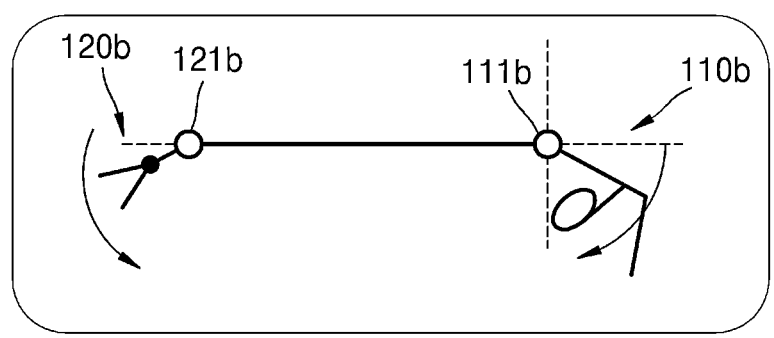
FIG. 1C is a conceptual diagram of a pitch operation of another conventional surgical instrument.
Figure 1D:
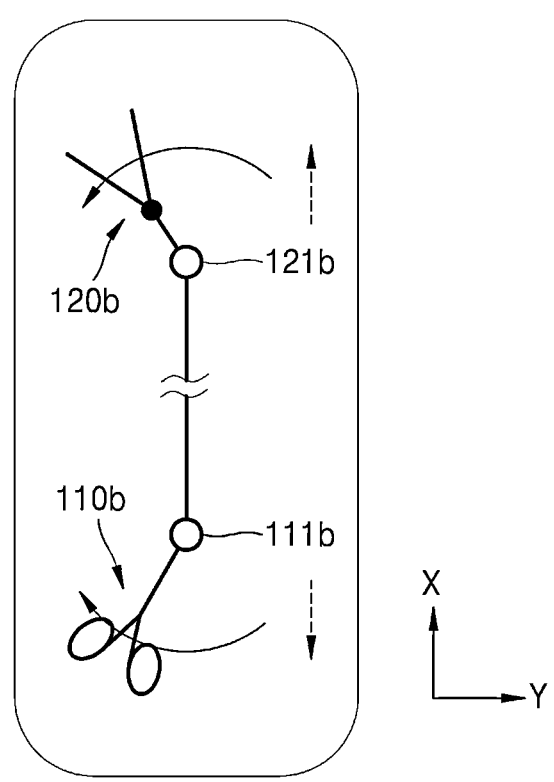
FIG. 1D is a conceptual diagram of a yaw operation.

FIG. 1C is a schematic view illustrating a pitch motion of another instrument for surgery of the related art, and FIG. 1D is a schematic view illustrating a yaw motion of the instrument for surgery of the related art.

Figure 1E:
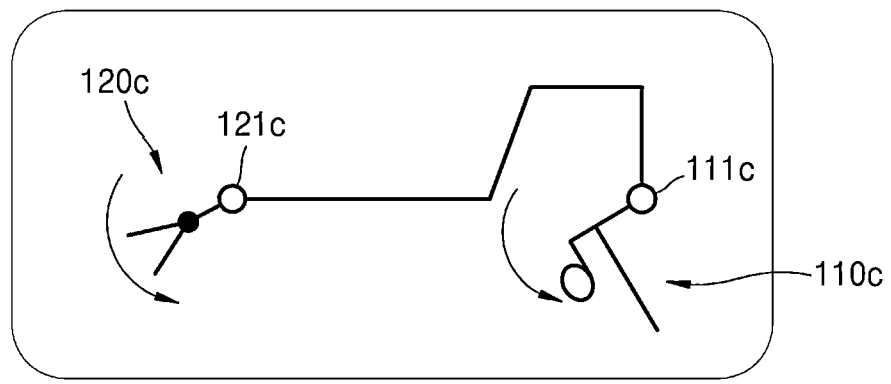
FIG. 1E is a conceptual diagram of a pitch operation of surgical instrument according to the present disclosure.
Figure 1F:
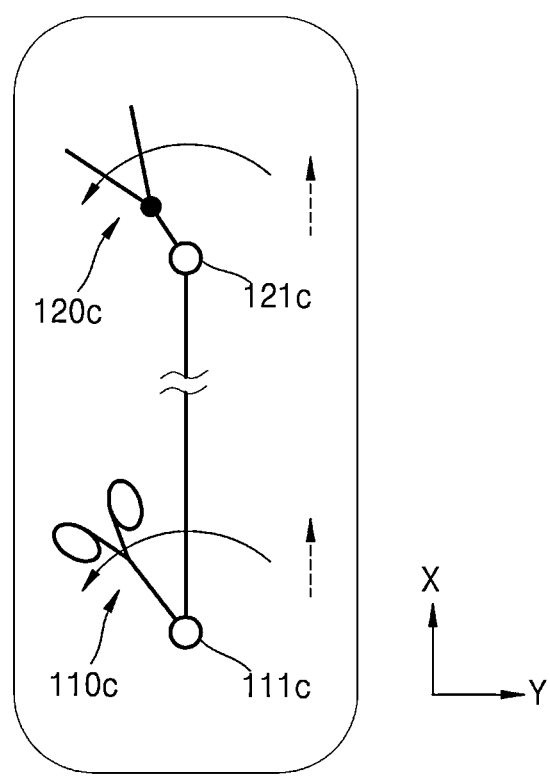
FIG. 1F is a conceptual diagram of a yaw operation.

Referring to FIG. 1C, some instruments for surgery of the related art have a mirror-symmetric structure and perform a pitch motion as follows: in a state in which an end tool 120b is formed in front of an end tool rotation center 121b and an manipulation part 110b is formed in back of a manipulation part rotation center 111b, when the manipulation part 110b is rotated clockwise, the end tool 120b is rotated counterclockwise, and when the manipulation part 110b is rotated counterclockwise, the end tool 120b is rotated clockwise. In this case, from the viewpoint of the rotation directions of the manipulation part 110b and the end tool 120b, the direction in which a user rotates the manipulation part 110b is opposite the direction in which the end tool 120b is accordingly rotated. Consequently, the user may confuse manipulation directions, and the operation of a joint may not be intuitive, thereby causing mistakes. In addition, referring to FIG. 1D, a yaw motion is performed as follows. In a state in which the end tool 120b is in front of the end tool rotation center 121b and the manipulation part 110b is in back of the manipulation part rotation center 111b, if the manipulation part 110b is rotated clockwise, the end tool 120b is rotated counterclockwise, and if the manipulation part 110b is rotated counterclockwise, the end tool 120b is rotated clockwise. In this case, from the viewpoint of the rotation directions of the manipulation part 110b and the end tool 120b, the direction in which a user rotates the manipulation part 110b is opposite the direction in which the end tool 120b is accordingly rotated. Consequently, the user may confuse manipulation directions, and the operation of the joint may not be intuitive, thereby causing mistakes. As described above, when a user performs a pitch or yaw motion of an instrument for surgery of the related art, the manipulation direction of the user is not the same as the operation direction of an end tool from the viewpoint of the rotation directions or the horizontal direction. This is because an end tool and a manipulation part of an instrument for surgery of the related art have different joint structures. That is, the end tool is formed in front of the rotation center of the end tool, whereas the manipulation part is formed in back of the rotation center of the manipulation part. In order to address this problem, instruments for surgery according to embodiments of the present disclosure illustrated in FIGS. 1E and 1F are characterized in that an end tool 120c is provided in front of an end tool rotation center 121c and a manipulation part 110c is also provided in front of a manipulation part rotation center 111c, such that the operations of the manipulation part 110c and the end tool 120c are intuitively identical to each other. In other words, unlike the configuration example of the related art in which the manipulation part is adjacent to a user (i.e., distant from the end tool) based on a joint thereof as illustrated in FIGS. 1A, 1B, 1C, and 1D, the instruments for surgery according to the embodiments of the present disclosure illustrated in FIGS. 1E and 1F are configured such that at least a portion of the manipulation part may be more adjacent to the end tool based on a joint thereof (i.e., than the joint thereof is to the end tool) at at least a moment of manipulation.

In other words, in the case of an instrument for surgery of the related art as illustrated in FIGS. 1A, 1B, 1C, and 1D, since an end tool is located in front of a rotation center thereof but a manipulation part is located in back of a rotation center thereof, the end tool fixed at a rear side thereof and configured to be moved at a front side thereof is moved by the manipulation part fixed at a front side thereof and configured to be moved at a rear side thereof, and thus the structures of the manipulation part and the end tool are not intuitively identical to each other. Therefore, the manipulation of the manipulation part and the operation of the end tool are not identical to each other from the viewpoint of the horizontal direction or rotation directions, and thus a user may be confused and may not intuitively quickly manipulate the manipulation part, thereby making mistakes. However, in the case of the instruments for surgery according to the embodiments of the present disclosure, since each of the end tool and the manipulation part moves with respect to a rear rotation center thereof, it may be considered that the operations of the end tool and the manipulation part are structurally intuitively identical to each other. In other words, like the end tool having a portion movable based on the rear rotation center thereof, the manipulation part has a portion movable based on the rear rotation center thereof. Thus, it may be considered that the operations of the end tool and the manipulation part are structurally intuitively identical to each other. Consequently, a user may intuitively rapidly control the direction of the end tool, and the possibility that the user makes a mistake may be significantly reduced. A specific mechanism enabling this function will be described below.

Figure 2:
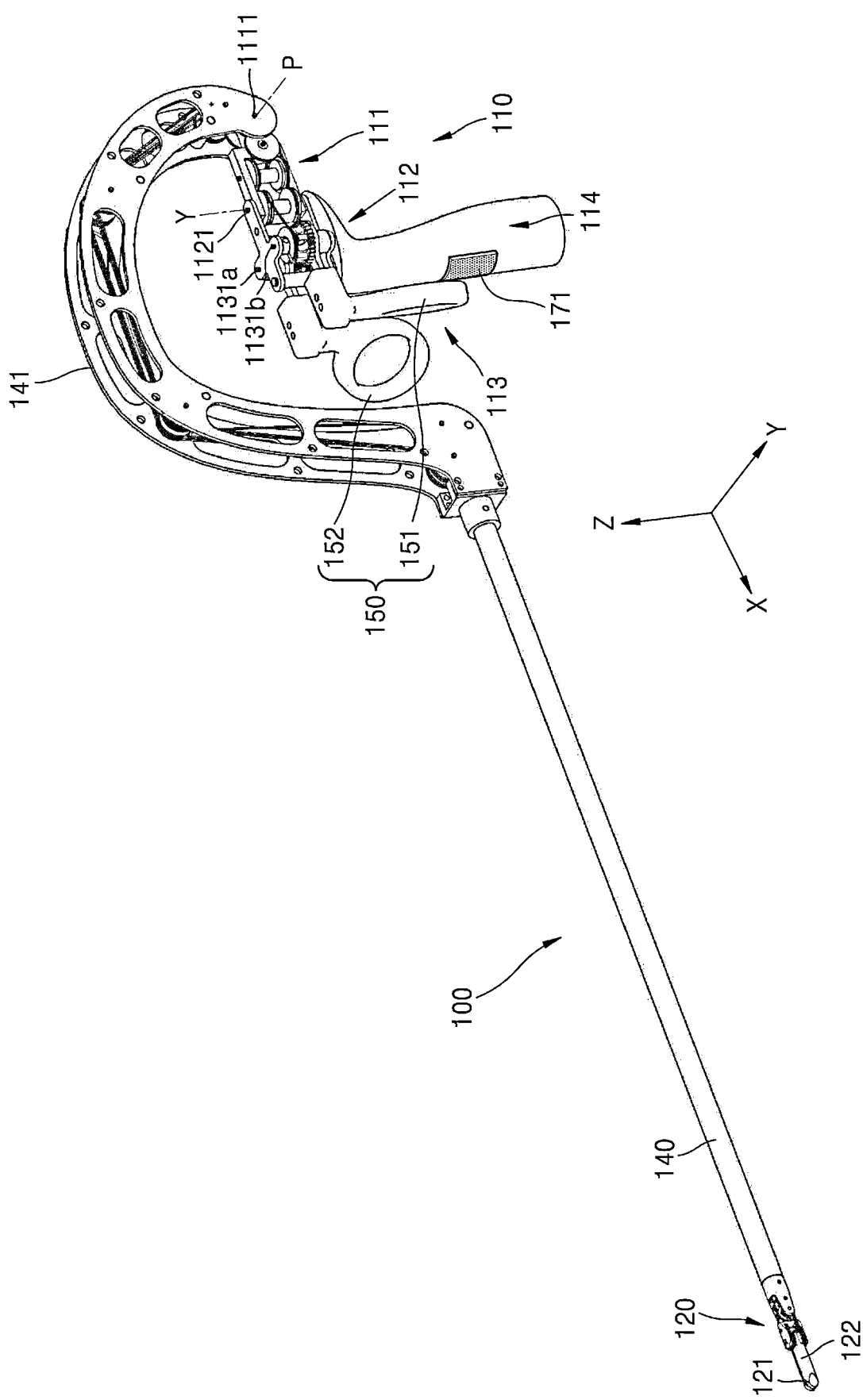
FIG. 2 is a perspective view illustrating surgical instrument according to a first embodiment of the present disclosure.
Figure 3:
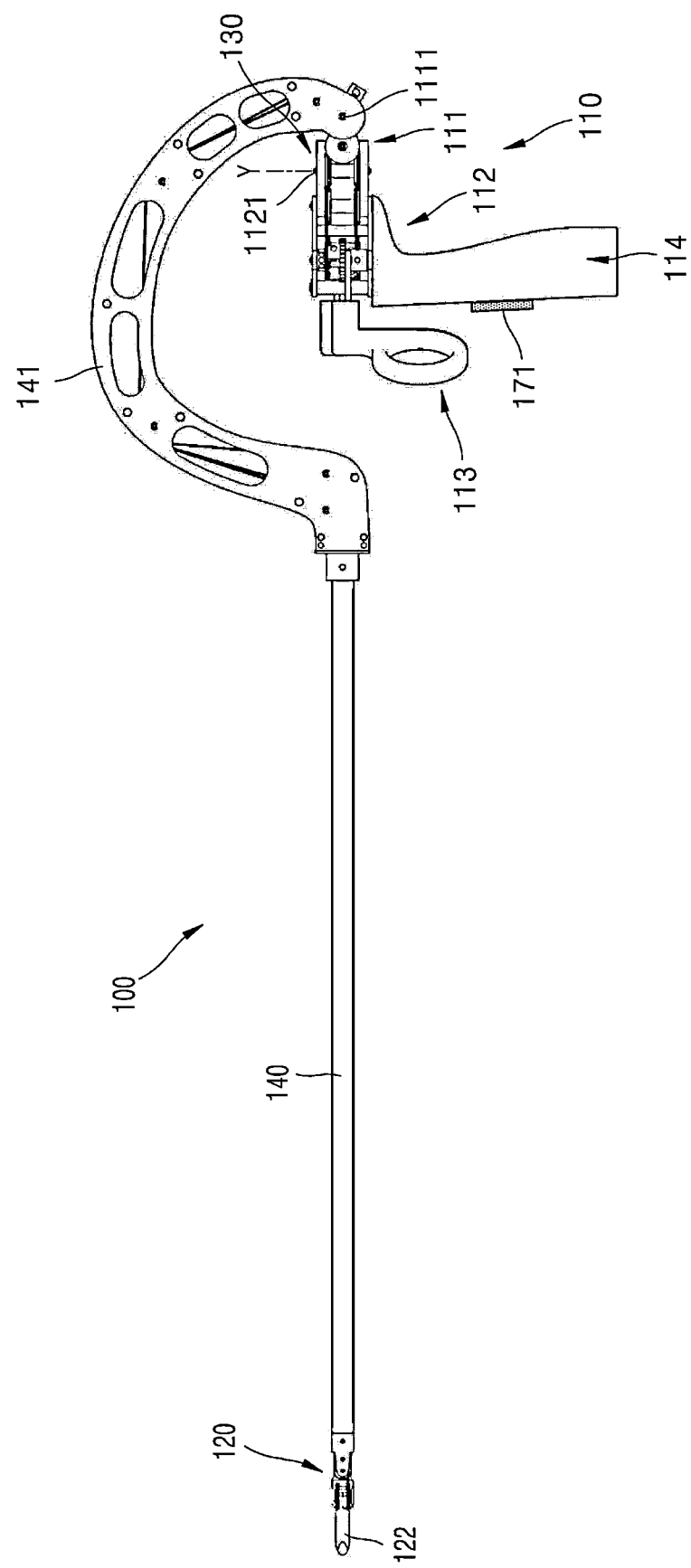
FIG. 3 is a side view of the surgical instrument of FIG. 2.

FIG. 2 is a perspective view illustrating an instrument for surgery according to a first embodiment of the present disclosure, and FIG. 3 is a side view illustrating the instrument for surgery shown in FIG. 2.

Referring to FIGS. 2, and 3, the instrument 100 for surgery according to the first embodiment of the present disclosure includes a manipulation part 110, an end tool 120, a power transmission part 130, a connecting part 140, and a ring handle 150. Here, the connecting part 140 may have a hollow shaft shape accommodating at least one wire (described later). The manipulation part 110 may be coupled to one end portion of the connecting part 140, and the end tool 120 may be coupled to the other end portion of the connecting part 140 such that the manipulation part 110 and the end tool 120 may be connected through the connecting part 140. Here, the connecting part 140 of the instrument 100 for surgery according to the first embodiment of the present disclosure is characterized by having a bent part 141 on a side of the manipulation part 110. As described above, an end portion of the connecting part 140 located on a side of the manipulation part 110 is bent such that a pitch manipulation part 111, a yaw manipulation part 112, and an actuation manipulation part 113 may be located on or adjacent to an extension line of the end tool 120. From another perspective, it may be stated that at least portions of the pitch manipulation part 111 and the yaw manipulation part 112 is accommodated in a concave region formed by the bent part 141. Owning to the shape of the bent part 141, the shapes and operations of the manipulation part 110 and the end tool 120 may be more intuitively identical to each other.

In addition, a plane formed by the bent part 141 may be substantially the same as a pitch plane, that is, an XZ plane shown in FIG. 2. In this manner, since the bent part 141 is provided on the same plane as the XZ plane, interference between manipulation parts may be reduced. Alternatively, any other configuration of the end tool and the manipulation part may be possible in addition to the XZ plane configuration.

The manipulation part 110 is provided on one end portion of the connecting part 140 and has an interface such as a tweezers shape, a stick shape, or a lever shape that a surgeon may directly manipulate, such that if an surgeon manipulates the interface, the end tool 120 connected to the interface and inserted into the body of a patient may be operated for surgery. Although FIG. 2 illustrates that the manipulation part 110 has a handle shape configured to be rotated by inserting a finger thereinto, the idea of the present disclosure is not limited thereto. That is, the manipulation part 110 may have any shape as long as the end tool 120 is connected to the manipulation part 110 and manipulated using the manipulation part 110.

The end tool 120 is provided on the other end portion of the connecting part 140 and is configured to be moved for surgery in a state in which that end tool 120 is inserted into a surgical site. As an example of the end tool 120, a pair of jaws 121 and 122 for gripping may be used as illustrated in FIG. 2. However, the idea of the present disclosure is not limited thereto. That is, various devices for surgery may be used as the end tool 120. For example, a device such as a one-armed cauter may be used as the end tool 120. The end tool 120 is connected to the manipulation part 110 through the power transmission part 130 to receive a driving force of the manipulation part 110 through the power transmission part 130, thereby performing a necessary surgical motion such as gripping, cutting, or suturing.

Herein, the end tool 120 of the instrument 100 for surgery of the first embodiment of the present disclosure is configured to rotate in at least two directions. For example, the end tool 120 may be capable of pitch motion around a Y axis of FIG. 2 and yaw motion and actuation motion around a Z axis of FIG. 2.

In the present disclosure, pitch, yaw, and actuation motions are defined as follows.

First, the pitch motion refers to upward and downward rotations of the end tool 120 with respect to an extension direction (the direction of an X axis in FIG. 2) of the connecting part 140, that is, rotation of the end tool 120 around the Y axis in FIG. 2. In other words, the pitch motion refers to upward and downward rotations of the end tool 120, which extends from the connecting part 140 in the extension direction (the X-axis direction in FIG. 2) of the connecting part 140, around the Y axis with respect to the connecting part 140. Next, the yaw motion refers to leftward and rightward rotations of the end tool 120 with respect to the extension direction (the X-axis direction in FIG. 2) of the connecting part 140, that is, rotation of the end tool 120 around the Z axis in FIG. 2. In other words, the yaw motion refers to leftward and rightward rotations of the end tool 120, which extends from the connecting part 140 in the extension direction (the X-axis direction in FIG. 2) of the connecting part 140, around the Z axis with respect to the connecting part 140. That is, the yaw motion refers to a motion in which the two jaws 121 and 122 of the end tool 120 are rotated around the Z axis in the same direction. In addition, the actuation motion refers to a motion in which the end tool 120 rotates around the same rotation axis as the yaw motion but the two jaws 121 and 122 rotate in opposite directions to move close to each other or away from each other. That is, the actuation motion refers to a motion in which the two jaws 121 and 122 rotate around the Z axis in opposite directions.

The power transmission part 130 may connect the manipulation part 110 and the end tool 120 to each other and transmit a driving force of the manipulation part 110 to the end tool 120. The power transmission part 130 may include a plurality of wires, pulleys, links, nodes, and gears. According to the embodiment of the present disclosure, the power transmission part 130 of the instrument 100 for surgery may include a pitch wire 130P, a first jaw wire 130J1, and a second jaw wire 130J2.

The ring handle 150 includes a first ring handle 151 and a second ring handle 152, Hereinafter, parts of the instrument 100 for surgery shown in FIG. 2 such as the manipulation part 110, the end tool 120, and the power transmission part 130 will be described in more detail.

(End Tool)

Figure 4:
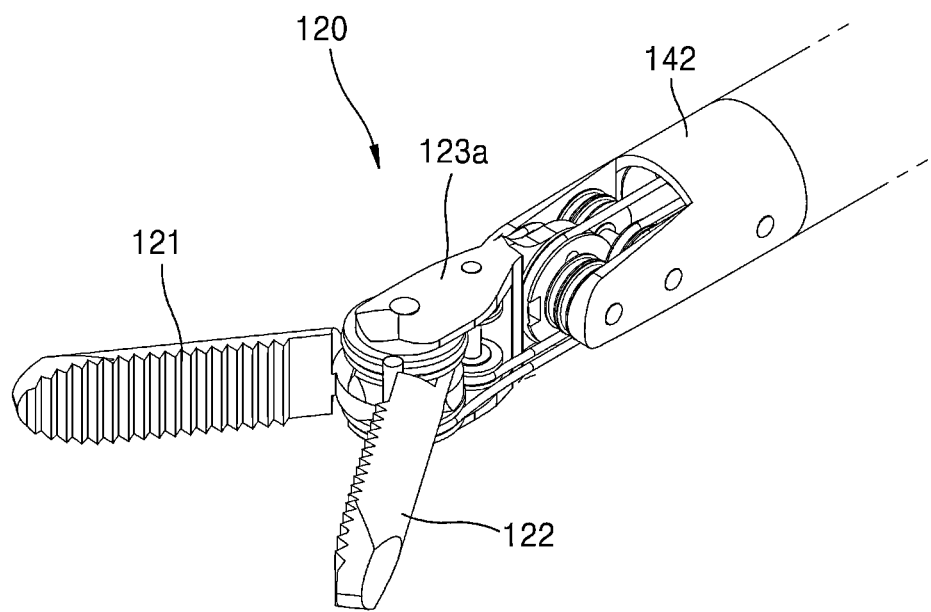
FIGS. 4 and 5 are perspective views illustrating an end tool of the surgical instrument of FIG. 2.
Figure 5:
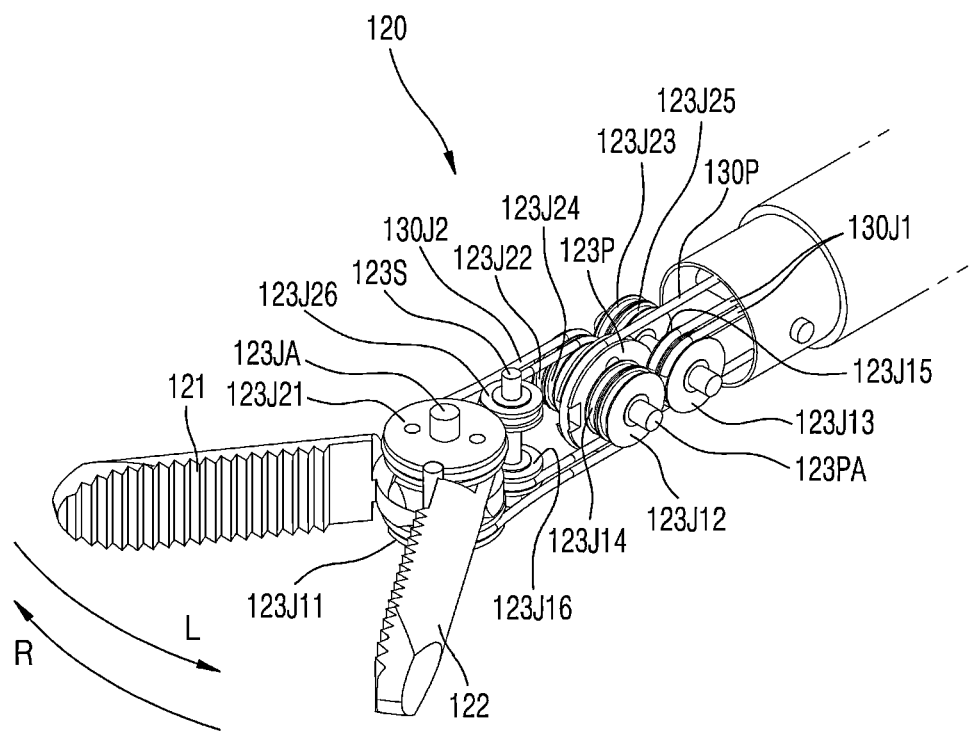
Figure 6:
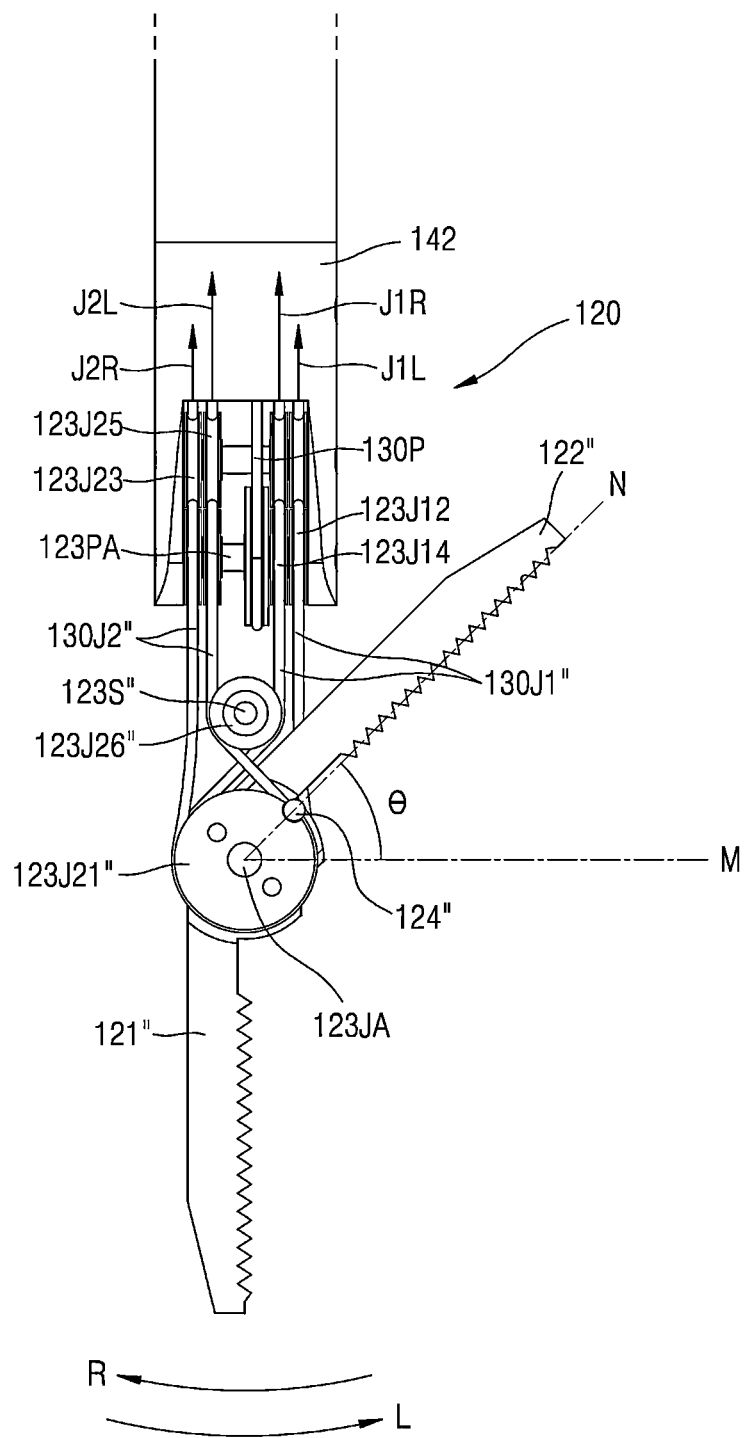
FIG. 6 is a plan view illustrating an end tool of the surgical instrument of FIG. 2.

Referring to FIGS. 4, 5 and 6, the end the end tool 120 of the first embodiment of the present disclosure includes a pair of jaws 121 and 122, that is, a first jaw 121 and a second jaw 122 for gripping motion. In addition, the end tool 120 includes: a J11 pulley 123J11, a J12 pulley 123J12, a J13 pulley 123J13, a J14 pulley 123J14, and a J15 pulley 123J15 that are related to the rotation motion of the first jaw 121; and a J21 pulley 123J21, a J22 pulley 123J22, a J23 pulley 123J23, a J24 pulley 123J24, and a J25 pulley 123J25 that are related to the rotation motion of the second jaw 122. In this case, the first jaw 121, the J11 pulley 123J11, the J12 pulley 123J12, the J14 pulley 123J14, the second jaw 122, the J21 pulley 123J21, the J22 pulley 123J22, and the J24 pulley 123J24 may be configured to rotate around an end tool pitch rotation shaft 123PA.

In addition, A connecting part hub 142 is provided on an end portion of the connecting part 140 coupled to the end tool 120. The J12 pulley 123J12, the J13 pulley 123J13, the J14 pulley 123J14, the J15 pulley 123J15, the J22 pulley 123J22, the J23 pulley 123J23, the J24 pulley 123J24, and the J25 pulley 123J25 are connected to the connecting part hub 142.

Although it is illustrated that pulleys facing each other are parallel to each other, the idea of the present disclosure is not limited thereto. That is, the pulleys may have various positions and sizes suitable for the configuration of the end tool.

The J11 pulley 123J11 and the J21 pulley 123J21 face each other and rotate independently around a jaw rotation shaft 123JA. Here, the first jaw 121 may be fixedly coupled to the J11 pulley 123J11 so as to be rotated together with the J11 pulley 123J11, and the second jaw 122 may be fixedly coupled to the J21 pulley 123J21 so as to be rotated together with the J21 pulley 123J21. Yaw and actuation motions of the end tool 120 are performed as according to rotations of the J11 pulley 123J11 and the J21 pulley 123J21. That is, yaw motion is performed when the J11 pulley 123J11 and the J21 pulley 123J21 are rotated in the same direction, and actuation motion is performed when the J11 pulley 123J11 and the J21 pulley 123J21 are rotated in opposite directions.

In addition, a J16 pulley 123J16 and a J26 pulley 123J26 may be additionally provided as auxiliary pulleys on a side of the J11 pulley 123J11 and the J21 pulley 123J21, and the auxiliary pulleys may be rotatable on an auxiliary pulley shaft 123S. Although it is illustrated that the J16 pulley 123J16 and the J26 pulley 123J26 are configured to rotate on the single auxiliary pulley shaft 123S, the auxiliary pulleys may be configured to rotate on separate shafts, respectively. In other words, the J16 pulley 123J16 being an auxiliary pulley may be placed between the J11 pulley 123J11 and the J12 pulley 123J12/the J14 pulley 123J14. In addition, the J26 pulley 123J26 being an auxiliary pulley may be placed between the J21 pulley 123J21 and the J22 pulley 123J22/ the J24 pulley 123J24. The auxiliary pulleys will be described later in more detail.

Elements related to rotation of the J11 pulley 123J11 will be described below.

The J12 pulley 123J12 and the J14 pulley 123J14 are placed to face each other at a side of the J11 pulley 123J11. In this case, the J12 pulley 123J12 and the J14 pulley 123J14 are independently rotatable about the end tool pitch rotation shaft 123PA. In addition, the J13 pulley 123J13 and the J15 pulley 123J15 are placed to face each other respectively at sides of the J12 pulley 123J12 and the J14 pulley 123J14. Here, the J13 pulley 123J13 and the J15 pulley 123J15 are independently rotatable around the Y-axis direction. Although it is illustrated that all of the J12 pulley 123J12, the J13 pulley 123J13, the J14 pulley 123J14, and the J15 pulley 123J15 are rotatable around the Y-axis direction, the idea of the present disclosure is not limited thereto, and the rotating axes of the respective pulleys may be oriented in various directions according to configurations thereof.

The first jaw wire 130J1 may be sequentially wound to make contact with at least portions of the J13 pulley 123J13, the J12 pulley 123J12, the J11 pulley 123J11, the J16 pulley 123J16, the J14 pulley 123J14, and the J15 pulley 123J15, and the first jaw wire 130J1 may move along the pulleys while rotating the pulleys.

Thus, when the first jaw wire 130J1 is pulled in the direction of an arrow J1R in FIG. 6, the first jaw wire 130J1 rotates the J15 pulley 123J15, the J14 pulley 123J14, the J16 pulley 123J16, the J11 pulley 123J11, the J12 pulley 123J12, and the J13 pulley 123J13. At this time, as the J11 pulley 123J11 is rotated in the direction of an arrow R in FIG. 6, the J11 pulley 123J11 rotates the first jaw 121.

On the other hand, when the first jaw wire 130J1 is pulled in the direction of an arrow J1L in FIG. 6, the first jaw wire 130J1 rotates the J13 pulley 123J13, the J12 pulley 123J12, the J11 pulley 123J11, the J16 pulley 123J16, the J14 pulley 123J14, and the J15 pulley 123J15. At this time, as the J11 pulley 123J11 is rotated in the direction of an arrow L in FIG. 6, the J11 pulley 123J11 rotates the first jaw 121.

Hereinafter, the auxiliary pulleys 123J16 and 123J26 will be described in more detail.

The auxiliary pulleys 123J16 and 123J26 may be in contact with the first jaw wire 130J1 and the second jaw wire 130J2, thereby changing paths of the first jaw wire 130J1 and the second jaw wire 130J2 to some degree and extending the rotation radii of the first jaw 121 and the second jaw 122. That is, according to the embodiment of the present disclosure, the auxiliary pulleys 123J16 and 123J26 are additionally provided such that the maximum rotation angle may be increased by θ as illustrated in FIG. 6. This allows the two jaws of the end tool 120 to move away from each other for actuation motion in a state in which the two jaws are rotated together by 90° in yaw motion in the direction L. That is, this is because it is possible to further rotate the second jaw 122 by an additional angle θ as illustrated in FIG. 6. Similarly, actuation motion is also possible in a state in which the two jaws are rotated in yaw motion in the direction R. In other words, owing to the auxiliary pulleys 123J16 and 123J26, the range of yaw motion in which actuation motion is possible may be increased. This will now be described in more detail.

In detail, in the instrument 100 for surgery according to the embodiment of the present disclosure, the J16 pulley 123J16 and the J26 pulley 123J26 are additionally arranged as auxiliary pulleys at a side of the J11 pulley 123J11 and the J21 pulley 123J21. In this manner, since the J16 pulley 123J16 and the J26 pulley 123J26 are arranged to change the paths of the first jaw wire 130J1 and the second jaw wire 130J2 to some degree and thus to change tangential directions of the first jaw wire 130J1 and the second jaw wire 130J2, a fixation coupling part of the second jaw wire 130J2 and the J21 pulley 123J21 may be rotated up to a line N of FIG. 6. That is, the fixation coupling part of the second jaw wire 130J2 and the J21 pulley 123J21 may be rotated until the coupling part is located on a common internal tangent of the J21 pulley 123J21 and the J26 pulley 123J26. Similarly, a coupling part of the first jaw wire 130J1 and the J11 pulley 123J11 may be rotated until the coupling part is located on an common internal tangent of the J11 pulley 123J11 and the J16 pulley 123J16, thereby extending the range of rotation in the direction R.

In this manner, according to the present disclosure, the rotation radii of the first jaw 121 and the second jaw 122 may be increased, thereby obtaining an effect of increasing the range of yaw motion in which actuation motion is normally performed for opening and closing.

Next, elements relating to the rotation of the J21 pulley 123J21 will be described.

The J22 pulley 123J22 and the J24 pulley 123J24 are placed to face each other at a side of the J21 pulley 123J21. Here, the J22 pulley 123J22 and the J24 pulley 123J24 are independently rotatable around the end tool pitch rotation shaft 123PA. In addition, the J23 pulley 123J23 and the J25 pulley 123J25 are placed to face each other at a side of the J22 pulley 123J22 and the J24 pulley 123J24. Here, the J23 pulley 123J23 and the J25 pulley 123J25 are independently rotatable around the Y-axis direction. Although it is illustrated that all of the J22 pulley 123J22, the J23 pulley 123J23, the J24 pulley 123J24, and the J25 pulley 123J25 are rotatable around the Y-axis direction, the idea of the present disclosure is not limited thereto, and the rotating axes of the respective pulleys may be oriented in various directions according to configurations thereof.

The second jaw wire 130J2 may be sequentially wound to make contact with at least portions of the J23 pulley 123J23, the J22 pulley 123J22, the J21 pulley 123J21, the J26 pulley 123J26, the J24 pulley 123J24, and the J25 pulley 123J25, and the second jaw wire 130J2 may move along the pulleys while rotating the pulleys.

Therefore, when the second jaw wire 130J2 is pulled in the direction of an arrow J2R of FIG. 6, the second jaw wire 130J2 rotates the J23 pulley 123J23, the J22 pulley 123J22, the J21 pulley 123J21, the J26 pulley 123J26, the J24 pulley 123J24, and the J25 pulley 123J25. At this time, as the J21 pulley 123J21 is rotated in the direction of the arrow R of FIG. 6, the J21 pulley 123J21 rotates the second jaw 122.

On the other hand, when the second jaw wire 130J2 is pulled in the direction of an arrow J2L of FIG. 6, the second jaw wire 130J2 rotates the J25 pulley 123J25, the J24 pulley 123J24, the J26 pulley 123J26, the J21 pulley 123J21, the J22 pulley 123J22, and the J23 pulley 123J23. At this time, as the J21 pulley 123J21 is rotated in the direction of the arrow L of FIG. 6, the J21 pulley rotates the second jaw 122.

In addition, if an end portion of the first jaw wire 130J1 is pulled in the direction of the arrow J1R of FIG. 6, and at the same time the other end portion of the first jaw wire 130J1 is pulled in the direction of the arrow J1L of FIG. 6 (that is, if both end portions of the first jaw wire 130J1 are pulled), since the first jaw wire 130J1 is wound around lower portions of the J12 pulley 123J12 and the J14 pulley 123J14 that are rotatable around the end tool pitch rotation shaft 123PA as shown in FIG. 5, the J11 pulley 123J11 to which the first jaw wire 130J1 is fixedly coupled, the first jaw 121, the jaw rotation shaft 123JA, and an end tool hub 123a, and the second jaw 122 connected thereto are all rotated counterclockwise around the end tool pitch rotation shaft 123PA, and as a result, the end tool 120 is rotated downward in pitch motion. At this time, since the second jaw 122 and the second jaw wire 130J2 fixedly coupled to the second jaw 122 is wound around upper portions of the J22 pulley 123J22 and the J24 pulley 123J24 that are rotatable around the end tool pitch rotation shaft 123PA, both end portions of the second jaw wire 130J2 are respectively moved in directions opposite the directions of the arrows J2L and J2R.

In contract, if an end portion of the second jaw wire 130J2 is pulled in the direction of the arrow J2R of FIG. 6, and at the same time the other end portion of the second jaw wire 130J2 is pulled in the direction of the arrow J2L of FIG. 6, since the second jaw wire 130J2 is wound around the upper portions of the J22 pulley 123J22 and the J24 pulley 123J24 that are rotatable around the end tool pitch rotation shaft 123PA as shown in FIG. 5, the J21 pulley 123J21 to which the second jaw 130J1 is fixedly coupled, the second jaw 122, the jaw rotation shaft 123JA, and the end tool hub 123a, and the first jaw 121 connected thereto are all rotated clockwise around the end tool pitch rotation shaft 123PA, and as a result, the end tool 120 is rotated upward in pitch motion. At this time, since the first jaw 121 and the first jaw wire 130J1 fixedly coupled to the first jaw 121 are wound around the lower portions of the J12 pulley 123J12 and the J14 pulley 123J14 that are rotatable around the end tool pitch rotation shaft 123PA, both end portions of the first jaw wire 130J1 are respectively moved in directions opposite the directions of the arrows J1L and J1R.

In addition, the end tool 120 of the instrument 100b for surgery may further include a pitch pulley 123P, the manipulation part 110 may further include a pitch wire end pulley 115P, and the power transmission part 130 may further include the pitch wire 130P. In detail, the pitch pulley 123P of the end tool 120 may be rotatable about the end tool pitch rotation shaft 123PA and may be fixedly coupled to the end tool hub 123a. In addition, a pitch pulley of the manipulation part may be rotatable about a pitch rotation shaft and may be fixedly coupled to a pitch manipulation part (not shown). In addition, the pitch wire 130P may connect the pitch pulley 123P of the end tool 120 to the pitch pulley of the manipulation part.

Thus, if a user rotates a first handle 114 around a pitch rotation shaft 1111 while holding the first handle 114 of the manipulation part 110, a pitch pulley coupled to the first handle 114 is rotated around the pitch rotation shaft 1111, and the rotation of the pitch pulley is transmitted to the pitch pulley 123P of the end tool 120 through the pitch wire 130P to rotate the pitch pulley 123P. As a result, the end tool 120 is rotated, and a pitch motion is performed.

That is, since the instrument 100 for surgery according to the first embodiment of the present disclosure includes the pitch pulley 123P of the end tool 120, the pitch wire end pulley 115P of the manipulation part 110, and the pitch wire 130P of the power transmission part 130, a pitch motion driving force of the pitch manipulation part 111 may be more completely transmitted to the end tool 120, and thus reliability of motion may be improved.

(Manipulation Part)

Figure 7:
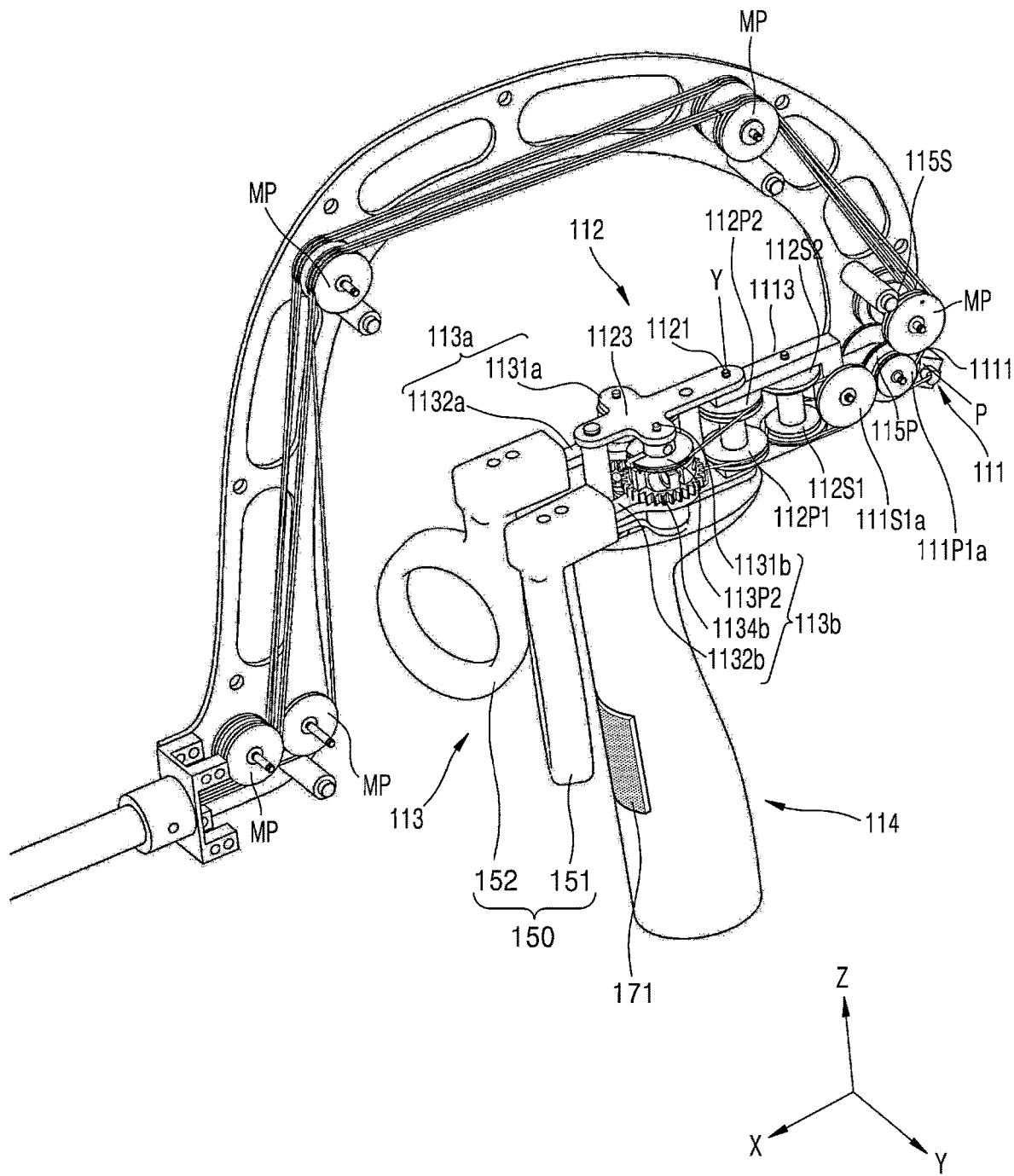
FIGS. 7 and 8 are perspective views illustrating a manipulation portion of the surgical instrument of FIG. 2.
Figure 8:
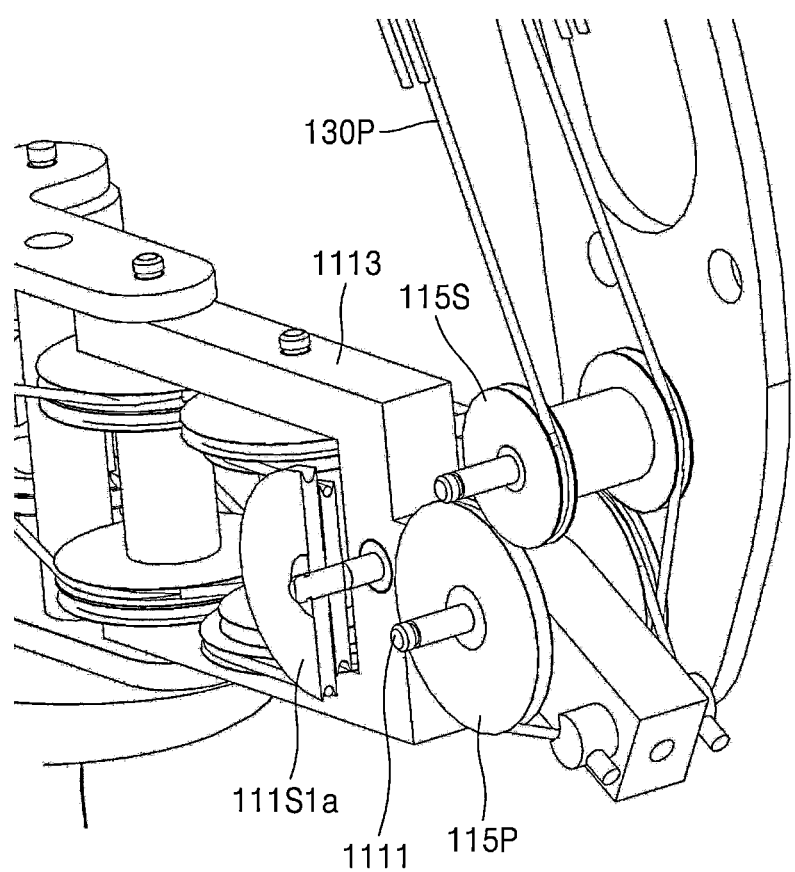

FIG. 7 and FIG. 8 are a perspective view illustrating the manipulation part of the instrument for surgery shown in FIG. 2.

Referring to FIG. 2 to FIG. 8, the manipulation part 110 of the instrument 100 for surgery includes the first handle 114 which a user may grip, the actuation manipulation part 113 configured to control actuation motion of the end tool 120, the yaw manipulation part 112 configured to control yaw motion of the end tool 120, and the pitch manipulation part 111 configured to control pitch motion of the end tool 120. In addition, the manipulation part 110 further includes the ring handle 150.

First, an example operation of the instrument 100 for surgery shown in FIG. 2 will be described. In a state in which a user holds the first handle 114 with his/her palm, the user may perform a pitch motion by rotating the first handle 114 around the Y axis (that is, around the pitch rotation shaft 1111) and a yaw motion by rotating the first handle 114 around the Z axis (that is, around a yaw rotation shaft 1121). In addition, in a state in which the user inserts his/her thumb and index finger in the ring handle 150 formed on an end of the actuation manipulation part 113, the user may rotate the actuation manipulation part 113 to perform an actuation motion.

Here, when the manipulation part 110 of the instrument 100 for surgery is rotated in a direction with respect to the connecting part 140, the end tool 120 is rotated intuitively in the same direction as the direction in which the manipulation part 110 is manipulated. In other words, if the first handle 114 of the manipulation part 110 is rotated in a certain direction, the end tool 120 is also rotated intuitively in the same direction as the certain direction, and thus a pitch motion or a yaw motion is performed. Here, the expression "intuitively in the same direction" may be used to denote that the direction in which a finger of a user holding the manipulation part 110 is moved is substantially the same as the direction in which a distal end portion of the end tool 120 is moved. The expression "intuitively in same direction" may not refer to completely in the same direction in a three-dimensional coordinate system. For example, it may be understood that the expression refers to sameness to the following extend: if a finger of a user is moved leftward, the distal end portion of the end tool 120 is also be moved leftward, and if the finger of the user is moved downward, the distal end portion of the end tool 120 is also moved downward.

To this end, in the instrument 100 for surgery of the first embodiment of the present disclosure, the manipulation part 110 and the end tool 120 are provided in the same direction with respect to a plane perpendicular to an extension axis (the X axis) of the connecting part 140. That is, when viewed based on a YZ plane of FIG. 2, the manipulation part 110 extends in a positive (+) X-axis direction, and the end tool 120 also extends in the positive (+) X-axis direction. In other words, it may be stated that the formation direction of the end tool 120 on an end portion of the connecting part 140 is the same as the formation direction of the manipulation part 110 on the other end portion of the connecting part 140 based on the YZ plane. Furthermore, in other words, it may be stated that the manipulation part 110 is located in a direction away from the body of a user holding the manipulation part 110, that is, in a direction in which the end tool 120 is provided. That is, in the case of parts such as the first handle 114 and actuation rotation parts 1132a and 1132b which a user holds and moves for actuation, yaw, and pitch motions, each moving portion extends from the rotation center of a corresponding joint for the motions in the positive (+) X-axis direction. In this manner, the manipulation part 110 may be configured like the end tool 120 in which each moving portion extends from the rotation center of a corresponding joint for the motions in the positive (+) X-axis direction, and as described with reference to FIG. 1, a manipulation direction of a user may be identical to an operation direction of the end tool from the viewpoint of rotation directions and leftward and rightward directions. As a result, intuitively the same manipulation may be performed.

In detail, in the case of an instrument for surgery of the related art, a direction in which a user manipulates a manipulation part is different from a direction in which the end tool is actually operated, that is, intuitively different from the direction in which the end tool is actually operated. Thus, surgeons may not easily intuitively manipulate the instrument for surgery and may spend a long time to learn a skill of operating the end tool in desired directions. In some cases, patients may suffer from malfunctions.

In order to solve such problems, the instrument 100 for surgery of the first embodiment of the present disclosure is configured such that the manipulation direction of the manipulation part 110 and the operation direction of the end tool 120 are intuitively identical to each other. To this end, the manipulation part 110 is configured like the end tool 120. That is, in the manipulation part 110, portions that are actually moved for actuation, yaw, and pitch motions extend respectively from rotation centers of corresponding joints in the positive (+) X-axis direction. This will now be described in more detail.

The first handle 114 may be configured such that a user may grip the first handle 114 with his/her hand. In particular, a user may grip the first handle 114 by holding around the first handle 114 with his/her palm. In addition, the actuation manipulation part 113 and the yaw manipulation part 112 are provided above the first handle 114, and the pitch manipulation part 111 is provided at a side of the yaw manipulation part 112. In addition, another end portion of the pitch manipulation part 111 is connected to the bent part 141 of the connecting part 140.

The actuation manipulation part 113 includes a first actuation manipulation part 113a and a second actuation manipulation part 113b. The first actuation manipulation part 113a includes a first actuation rotation shaft 1131a, a first actuation rotation part 1132a, a first actuation pulley 113P1, and a first actuation gear 1134a. The second actuation manipulation part 113b includes a second actuation rotation shaft 1131b, a second actuation rotation part 1132b, a second actuation pulley 113P2, and a second actuation gear 1134b. Here, the ring handle 150 may be further formed on ends of the first and second actuation rotation parts 1132a and 1132b and may function as second handles.

Here, the actuation rotation shafts 1131a and 1131b may make a predetermined angle with an XY plane on which the connecting part 140 is located. For example, the actuation rotation shafts 1131a and 1131b may be parallel with the Z axis. In this state, if the pitch manipulation part 111 or the yaw manipulation part 112 is rotated, the coordinate system of the actuation manipulation part 113 may be relatively varied. However, the idea of the present disclosure is not limited thereto, and the actuation rotation shafts 1131a and 1131b may be oriented in various directions according to ergonomic designs for the hand structure of a user holding the actuation manipulation part 113.

In addition, the first actuation rotation part 1132a, the first actuation pulley 113P1, and the first actuation gear 1134a may be fixedly coupled to each other so as to be rotated together around the first actuation rotation shaft 1131a. Here, the first actuation pulley 113P1 may include a single pulley or two pulleys fixedly coupled to each other.

Similarly, the second actuation rotation part 1132b, the second actuation pulley 113P2, and the second actuation gear 1134b may be fixedly coupled to each other so as to be rotated together around the second actuation rotation shaft 1131b. Here, the second actuation pulley 113P2 may include a single pulley or two pulleys fixedly coupled to each other.

Here, the first actuation gear 1134a and the second actuation gear 1134b may be engaged with each other, and thus if one of the first and second actuation gears 1134a and 1134b is rotated, the first and second actuation gears 1134a and 1134b may be rotated together in opposite directions.

On the other hand, in order to lock and unlock an actuation operation, a first coupling portion (see 1135 of FIG. 9) may be further formed in the actuation manipulation portion 113. The first coupling portion (see 1135 of FIG. 9) is fixedly coupled to at least a portion of the above-described second actuation rotating portion 1132b, the second actuation pulley 113P2 and the second actuation gear 1134b, so that may be formed to be rotatable together with the second actuation rotating portion, the second actuation pulley and the second actuation gear around a second actuation rotating axis 1131b.

Here, the first coupling portion (see 1135 of FIG. 9) may be formed in a pulley-shape (or a portion thereof), and an outer peripheral surface of the first coupling portion may be formed in a gear-shape having one or more cog wheels.

Figure 9:
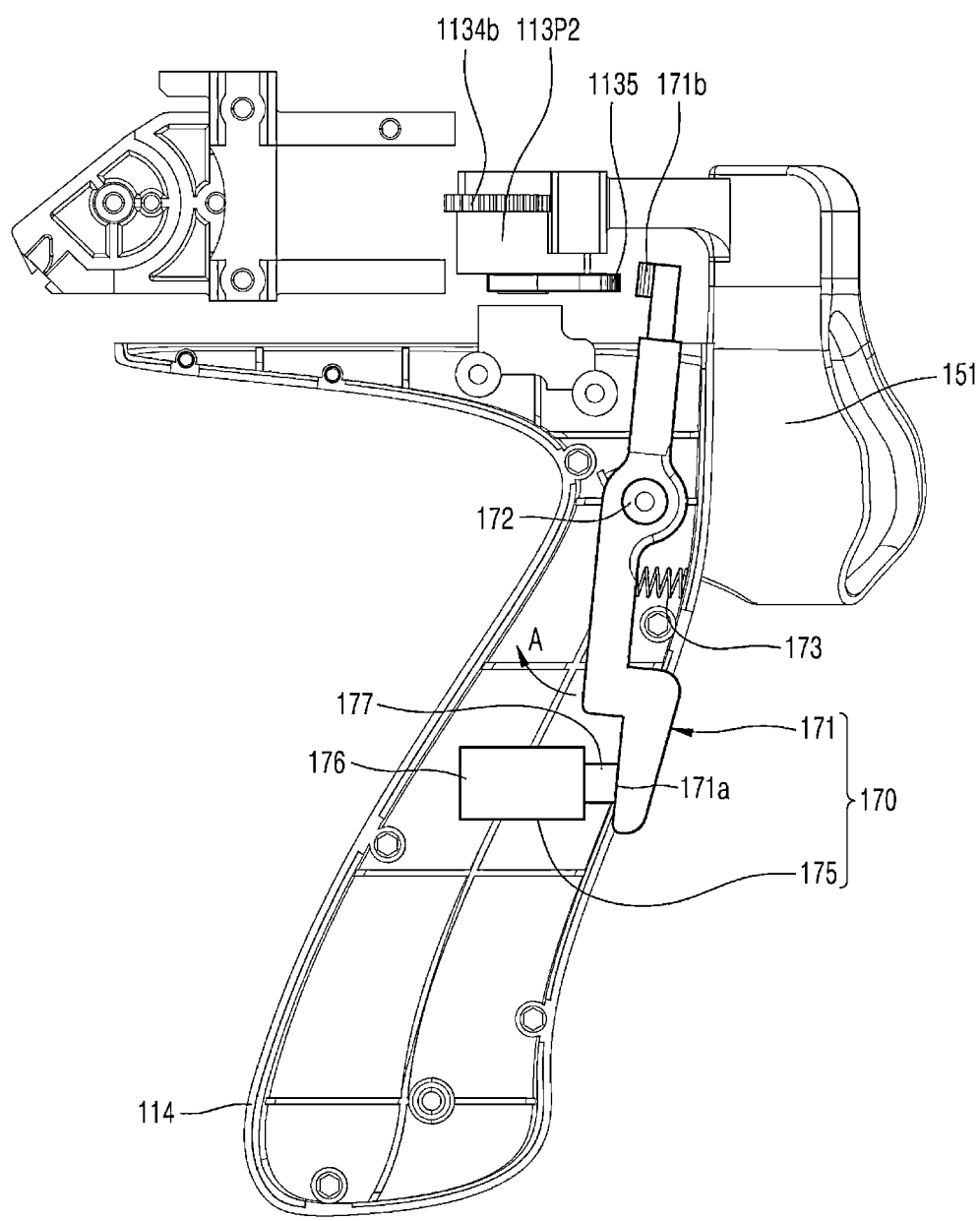
FIG. 9 is a side view illustrating an unlocking state of the surgical instrument of FIG. 2.

When a second coupling portion 171b of a locking device 170 to be described later in FIG. 9 is inserted into one of the cog wheels of the first coupling portion 1135, the actuation manipulation portion 113 is in a locked state in that state, and its movement is limited. In addition, when the second coupling portion 171b of the locking device 170 is spaced apart from the first coupling portion 1135, the actuation manipulation portion 113 is in an unlocked state so that it may rotate freely. This will be described in more detail later.

Here, the second actuation rotating axis 1131b, the second actuation rotating portion 1132b, the second actuation pulley 113P2, the second actuation gear 1134b and the first coupling portion (see 1135 of FIG. 9) may be formed as separate members, or at least some of these members may be formed as one body. For example, the second actuation rotating portion 1132b and the second actuation pulley 113P2 may be formed as one body, and the second actuation gear 1134b and the first coupling portion (see 1135 of FIG. 9) may be formed as one body.

The yaw manipulation part 112 may include a yaw rotation shaft 1121, a first jaw yaw pulley 112P1, a second jaw yaw pulley 112P2, and a yaw frame 1123. In addition, the yaw manipulation part 112 may further include a first jaw yaw auxiliary pulley 112S1 provided on a side of the first jaw yaw pulley 112P1, and a second jaw yaw auxiliary pulley 112S2 provided on a side of the second jaw yaw pulley 112P2. Here, the first jaw yaw auxiliary pulley 112S1 and the second jaw yaw auxiliary pulley 112S2 may be coupled to a pitch frame 1113 (described later).

In the drawings, it is illustrated that the yaw manipulation part 112 includes the first jaw yaw pulley 112P1 and the second jaw yaw pulley 112P2, and each of the first jaw yaw pulley 112P1 and the second jaw yaw pulley 112P2 includes two pulleys facing each other and independently rotatable. However, the idea of the present disclosure is not limited thereto. That is, according to the configuration of the yaw manipulation part 112, the yaw manipulation part 112 may include one or more pulleys having the same diameter or different diameters.

Specifically, the yaw rotation shaft 1121 is provided on a side of the actuation manipulation part 113 above the first handle 114. In this case, the first handle 114 is rotatable around the yaw rotation shaft 1121.

Here, the yaw rotation shaft 1121 may make a predetermined angle with the XY plane in which the connecting part 140 is provided. For example, the yaw rotation shaft 1121 may be oriented in a direction parallel to the Z axis, and in this state, if the pitch manipulation part 111 is rotated, the coordinate system of the yaw rotation shaft 1121 may be relatively varied as described above. However, the idea of the present disclosure is not limited thereto, and the yaw rotation shaft 1121 may be oriented in various directions according to ergonomic designs for the hand structure of a user holding the manipulation part 110.

In addition, the first jaw yaw pulley 112P1 and the second jaw yaw pulley 112P2 are coupled to the yaw rotation shaft 1121 such that the first jaw yaw pulley 112P1 and the second jaw yaw pulley 112P2 may be rotated on the yaw rotation shaft 1121. In addition, the first jaw wire 130J1 may be wound around the first jaw yaw pulley 112P1, and the second jaw wire 130J2 may be wound around the second jaw yaw pulley 112P2. In this case, each of the first jaw yaw pulley 112P1 and the second jaw yaw pulley 112P2 may include two pulleys facing each other and independently rotatable. Therefore, an inward wire and an outward wire may be respectively wound around separate pulleys and thus may not interfere with each other.

The yaw frame 1123 connects the first handle 114, the yaw rotation shaft 1121, the first actuation rotation shaft 1131a, and the second actuation rotation shaft 1131b such that the first handle 114, the yaw manipulation part 112, and the actuation manipulation part 113 may be rotated together around the yaw rotation shaft 1121.

The pitch manipulation part 111 may include the pitch rotation shaft 1111, a first jaw pitch pulley-a 111P1a, a first jaw pitch pulley-b 111P1b, a second jaw pitch pulley-a 111P2a, a second jaw pitch pulley-b 111P2b, and the pitch frame 1113. In addition, the pitch manipulation part 111 may further include a first jaw pitch auxiliary pulley-a 111S1a provided at a side of the first jaw pitch pulley-a 111P1a, a first jaw pitch auxiliary pulley-b 111S1b provided at a side of the first jaw pitch pulley-b 111Pb, a second jaw pitch auxiliary pulley-a 111S2a provided at a side of the second jaw pitch pulley-a 111P2a, and a second jaw pitch auxiliary pulley-b 111S2b provided at a side of the second jaw pitch pulley-b 111P2b. The pitch manipulation part 111 is connected to a bent part 141 of a connecting part 140 through the pitch rotation shaft 1111.

In detail, the pitch frame 1113 serves as a base frame of the pitch manipulation part 111, and the yaw rotation shaft 1121 is rotatably coupled to an end portion of the pitch frame 1113. That is, the yaw frame 1123 is rotatable around the yaw rotation shaft 1121 with respect to the pitch frame 1113.

As described above, the yaw frame 1123 connects the first handle 114, the yaw rotation shaft 1121, the first actuation rotation shaft 1131a, and the second actuation rotation shaft 1131b to each other, and is also connected to the pitch frame 1113. Therefore, if the pitch frame 1113 is rotated around the pitch rotation shaft 1111, the yaw frame 1123, the first handle 114, the yaw rotation shaft 1121, the first actuation rotation shaft 1131a, and the second actuation rotation shaft 1131b connected to the pitch frame 1113 are rotated together. That is, if the pitch manipulation part 111 is rotated around the pitch rotation shafts 1111, the actuation manipulation part 113 and the yaw manipulation part 112 are rotated together with the pitch manipulation part 111. In other words, if a user rotates the first handle 114 around the pitch rotation shaft 1111, the actuation manipulation part 113, the yaw manipulation part 112, and the pitch manipulation part 111 are moved together.

The pitch manipulation part 111, the first jaw pitch pulley-a 111P1a, the first jaw pitch pulley-b 111P1b, the second jaw pitch pulley-a 111P2a, and the second jaw pitch pulley-b 111P2b are coupled to the pitch frame 1113. In this case, the first jaw pitch pulley-a 111P1a, the first jaw pitch pulley-b 111P1b, the second jaw pitch pulley-a 111P2a, and the second jaw pitch pulley-b 111P2b are coupled to the pitch rotation shaft 1111 in a manner rotatable around the pitch rotation shaft 1111.

Here, the first jaw pitch pulley-a 111P1a and the first jaw pitch pulley-b 111P1b may face each other and may be independently rotated. Therefore, an inward wire and an outward wire may be respectively wound around separate pulleys and thus may not interfere with each other. Similarly, the second jaw pitch pulley-a 111P2a and the second jaw pitch pulley-b 111P2b may face each other and may be independently rotated. Therefore, an inward wire and an outward wire may be respectively wound around separate pulleys and thus may not interfere with each other.

Referring to FIG. 7, the pitch wire end pulley 115P is fixedly coupled to the pitch frame 1113 and rotatable together with the pitch frame 1113. In addition, the pitch wire 130P is fixedly coupled to the pitch frame 1113 through a pitch wire auxiliary pulley 115S and the pitch wire end pulley 115P. As a result, the pitch frame 1113 and the pitch wire end pulley 115P may be rotated together around the pitch rotation shaft 1111 by pitch rotation.

The pitch wire 130P is operated as follows.

The pitch pulley 123P is fixedly coupled to the end tool hub 123 of the end tool 120, and the manipulation part 110 includes the pitch wire end pulley 115P, wherein the pitch pulley 123P and the pitch wire end pulley 115P are connected to each other through the pitch wire 130P such that pitch motion of the end tool 120 may be easily performed by pitch-manipulating the manipulation part 110. Here, both ends of the pitch wire 130P are fixedly coupled to the pitch frame 1113 respectively through the pitch wire auxiliary pulley 115S and the pitch wire end pulley 115P, and the pitch wire end pulley 115P is also fixedly coupled to the pitch frame 1113. That is, the pitch frame 1113 and the pitch wire end pulley 115P are rotated together about the pitch rotation shaft 1111 by pitch rotation of the manipulation part, and as a result, both sides of the pitch wire 130P are also moved in opposite directions such that additional power for pitch rotation may be transmitted independently of pitch motion of the end tool by the first jaw wire 130J1 and the second jaw wire 130J2.

The first handle 114, the pitch manipulation part 111, the yaw manipulation part 112, and the actuation manipulation part 113 are connected as follows. The actuation rotation shafts 1131a and 1131b, the yaw rotation shaft 1121, and the pitch rotation shaft 1111 may be provided on the first handle 114. In this case, since the actuation rotation shafts 1131a and 1131b are directly provided on the first handle 114, and the first handle 114 and the actuation manipulation part 113 may be directly connected to each other. In addition, since the yaw rotation shaft 1121 is directly provided on the first handle 114, the first handle 114 and the yaw manipulation part 112 may be directly connected to each other. However, since the pitch manipulation part 111 is provided at a side of the yaw manipulation part 112 and connected to the yaw manipulation part 112, the pitch manipulation part 111 may not be directly connected to the first handle 114 but may be indirectly connected to the first handle 114 through the yaw manipulation part 112.

Referring to the drawings, in the instrument 100 for surgery according to the first embodiment of the present disclosure, the pitch manipulation part 111 and the end tool 120 may be provided on the same axis or on parallel axes (to the X axis). That is, the pitch rotation shaft 1111 of the pitch manipulation part 111 is provided on an end portion of the bent part 141 of the connecting part 140, and the end tool 120 is provided on the other end portion of the connecting part 140.

In addition, one or more relay pulleys MP may be placed on a middle portion of the connecting part 140, particularly, on the bent part 141 of the connecting part 140 to change paths of wires or guide wires. At least portions of wires may be wound around the relay pulleys MP, thereby guiding paths of the wires and arranging the wires along a bent shape of the bent part 141.

In the drawings, it is illustrated that the connecting part 140 includes the bent part 141 and has a curved shape with a predetermined radius of curvature. However, the idea of the present disclosure is not limited thereto. If necessary, the connecting part 140 may have a straight shape or may be bent at least one time, and even in this case, it may be stated that the pitch manipulation part 111 and the end tool 120 are provided substantially on the same axis or parallel axes. In addition, although FIG. 3 illustrates that the pitch manipulation part 111 and the end tool 120 are provided on an axis parallel to the X axis, the idea of the present disclosure is not limited thereto. For example, the pitch manipulation part 111 and the end tool 120 may be provided on different axes.

(Locking Device)

Hereinafter, the locking device 170 of the surgical instrument 1 according to an embodiment of the present disclosure will be described in more detail.

Figure 10:
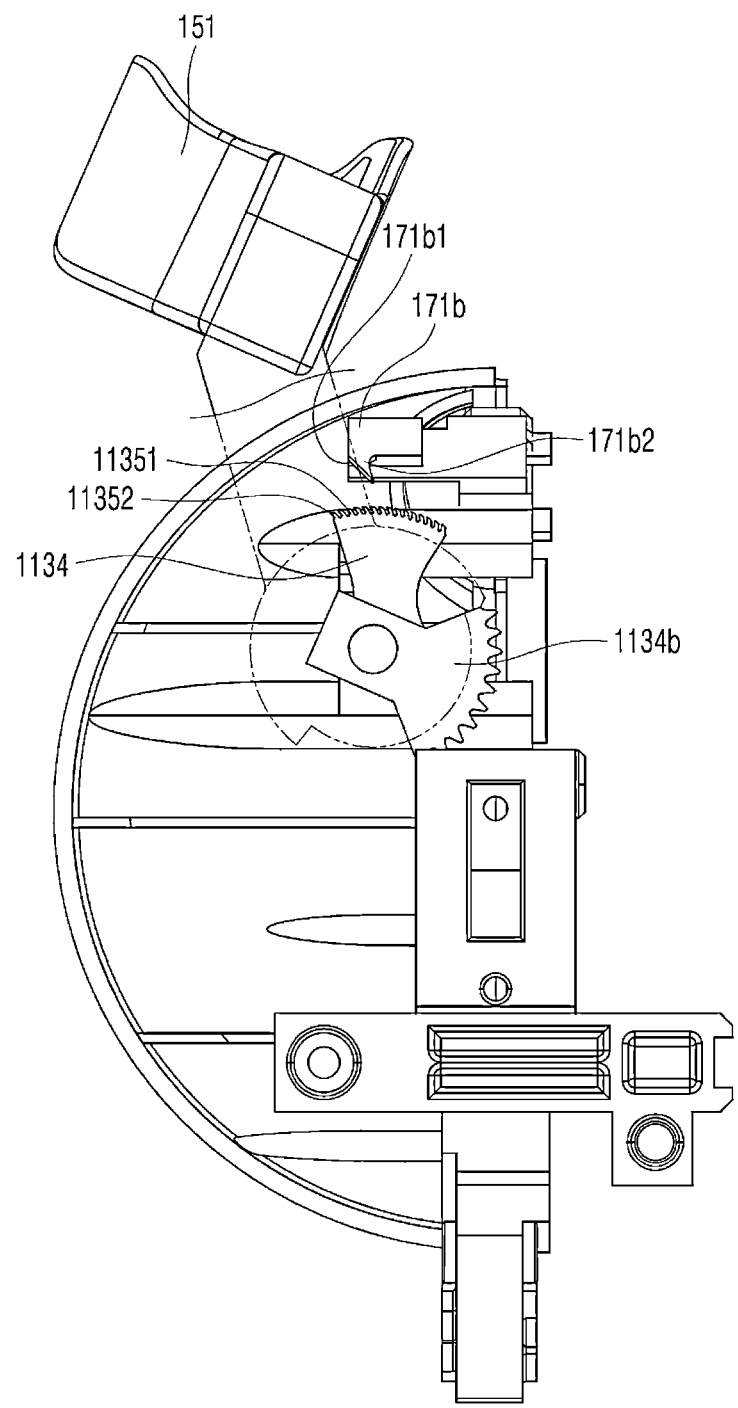
FIG. 10 is a plan view illustrating an unlocking state of the surgical instrument of FIG. 2.
Figure 11:
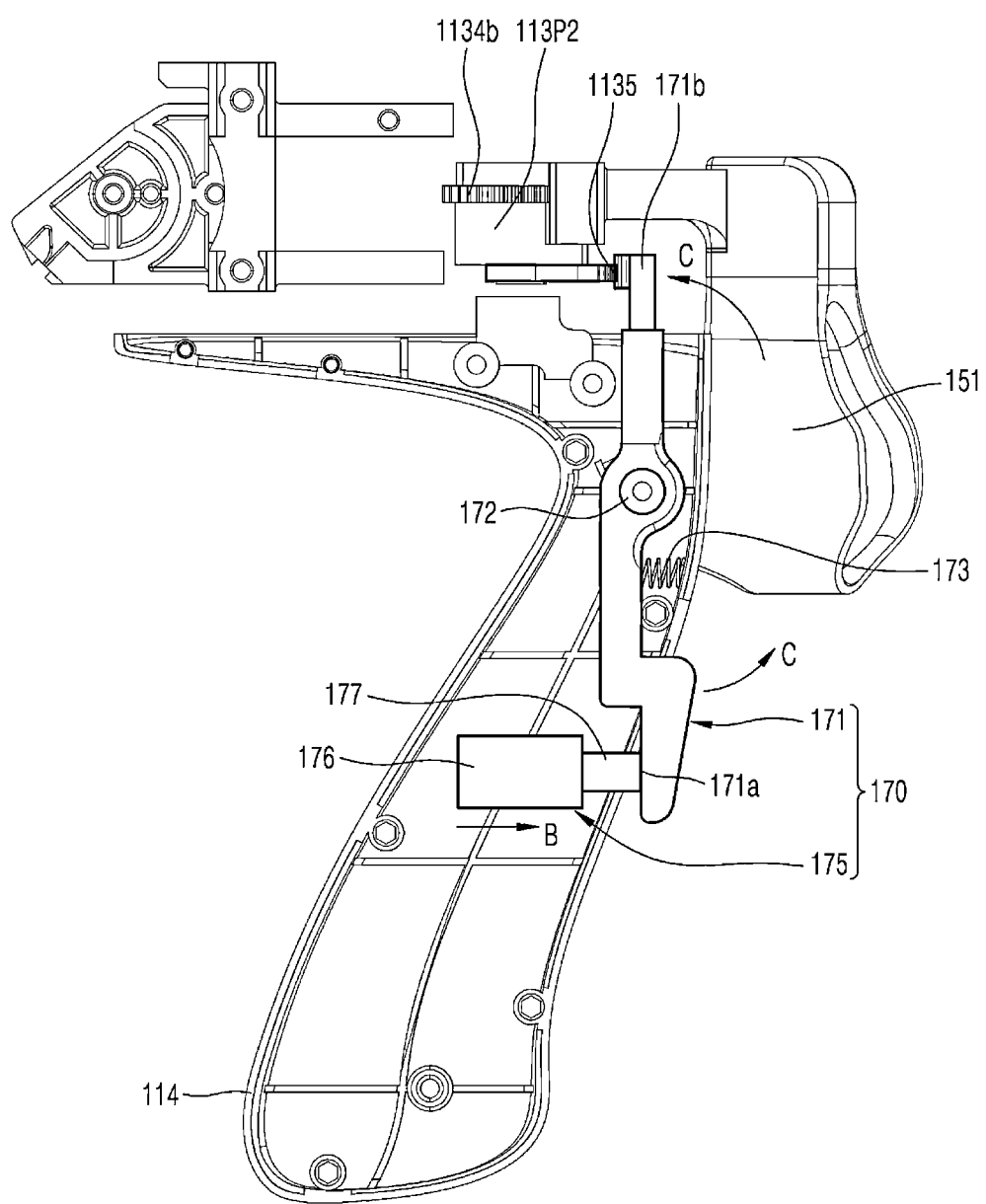
FIG. 11 is a side view illustrating a locking state of the surgical instrument of FIG. 2.
Figure 12:
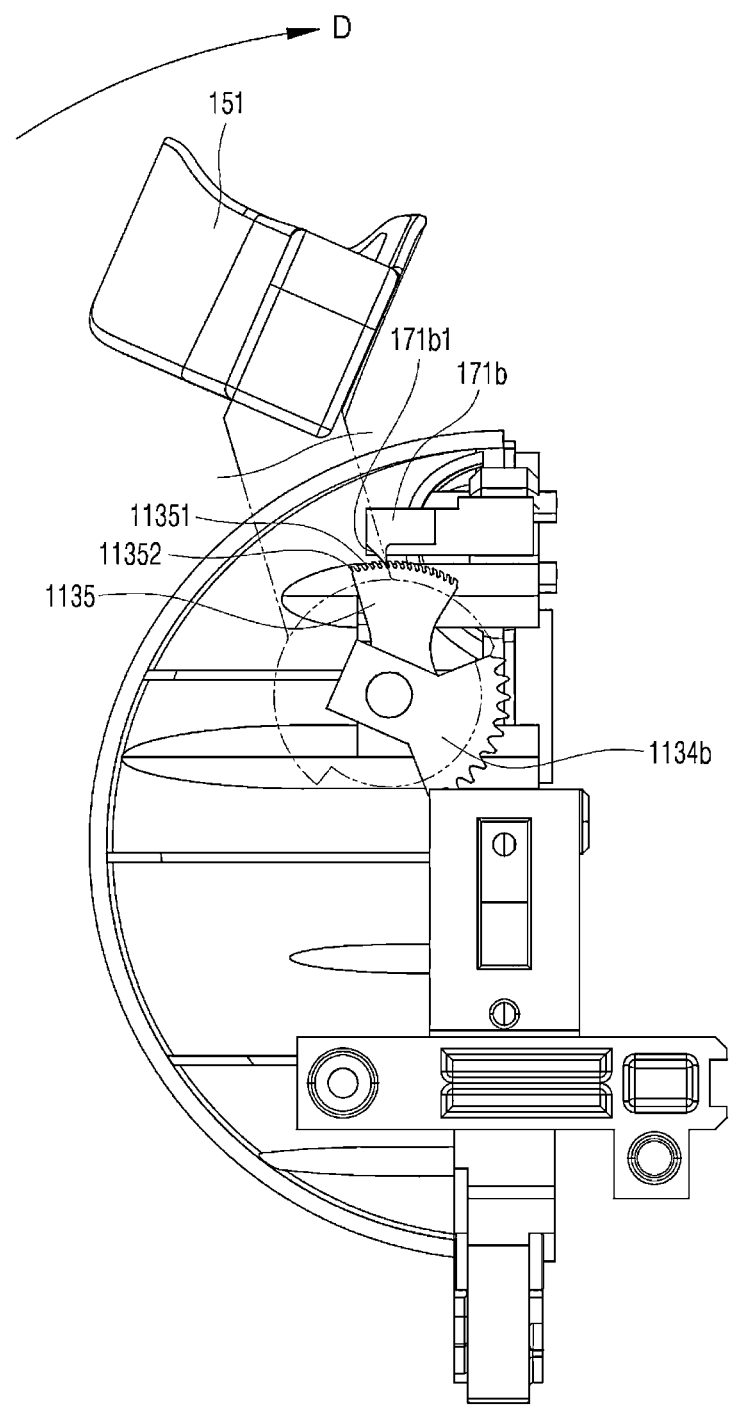
FIG. 12 is a plan view illustrating a locking state of the surgical instrument of FIG. 2.
Figure 13:
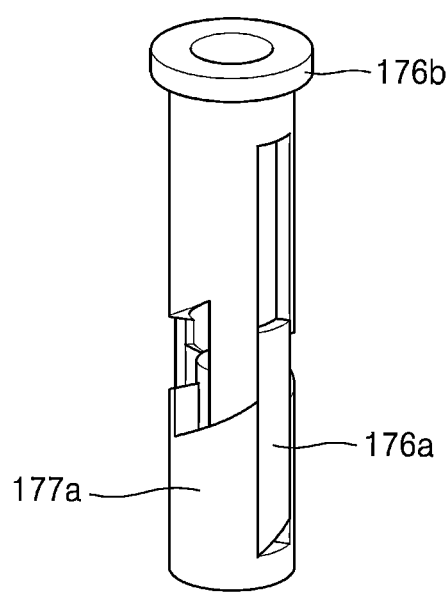
FIGS. 13 and 14 are diagrams illustrating a drawing in/drawing out mechanism of a pressing portion with respect to a body portion in a locking control portion of a locking device of FIG. 9.
Figure 14:
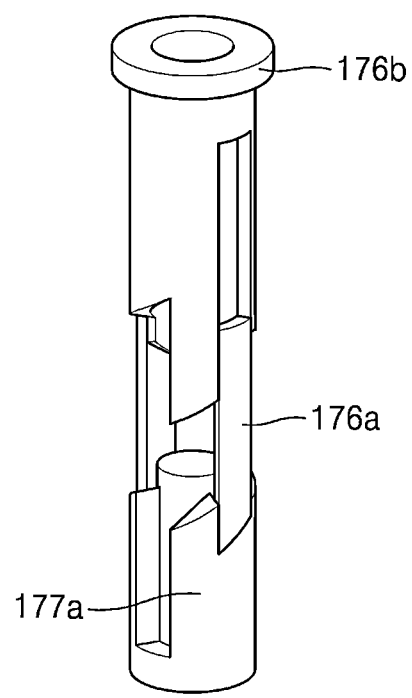

FIG. 9 is a side view illustrating an unlocking state of the surgical instrument of FIG. 2, and FIG. 10 is a plan view illustrating an unlocking state of the surgical instrument of FIG. 2. FIG. 10 is a side view illustrating a locking state of the surgical instrument of FIG. 2, and FIG. 11 is a plan view illustrating a locking state of the surgical instrument of FIG. 2. FIGS. 13 and 14 are diagrams illustrating a drawing in/drawing out mechanism of a pressing portion with respect to a body portion in a locking control portion of a locking device of FIG. 9. Here, for convenience of explanation, FIGS. 10 and 12 are illustrated with the second actuation rotating portion (1132b in FIG. 7) and the second actuation pulley (113P2 in FIG. 7) omitted, and some drawings are illustrated with some components omitted.

Referring to FIGS. 9 to 14, the locking device 170 may include a locking portion 171 and a locking control portion 175. Such the locking device 170 is formed to be able to be in contact with the actuation manipulation portion 113, and performs a role of locking or unlocking the actuation operation of the actuation manipulation portion 113.

In detail, the locking portion 171 is formed in a long rod-shape, and is formed to be rotatable around a locking rotating shaft 172 formed in a first handle 114. A contact portion 171a in contact with the locking control portion 175 is formed at one end of the locking portion 171, and the second coupling portion 171b capable of contacting the first coupling portion 1135 of the actuation manipulation portion 113 may be formed at the other end of the locking portion 171. Here, the second coupling portion 171b may be formed to engage the first coupling portion 1135 of the actuation manipulation portion 113 described above. Here, the second coupling portion 171b may be formed as a hook-shape, and may be formed to be able to engage with each cog wheel of the first coupling portion 1135 to be described later.

Here, in the second coupling portion 171b, one surface 1171b1 may be formed to have a predetermined angle and a gentle inclination, and the other surface 171b2 may be formed to be vertical or nearly vertical. Similarly, in the first coupling portion 1135 of the actuation manipulation portion 113, one surface 11351 may be formed to have a predetermined angle and a gentle inclination, and the other surface 11352 may be formed vertically or nearly vertical. In this case, the inclined one surface 171b1 of the second coupling portion 171b and the inclined one surface 11351 of the first coupling portion 1135 may be disposed to face each other (i.e., abut). By such a configuration, in a state in which the second coupling portion 171b and the first coupling portion 1135 are coupled (or engaged) to each other, they act as a kind of ratchet, and only rotation in one direction may be possible.

That is, in a state in which the second coupling portion 171b and the first coupling portion 1135 are coupled to each other, when a user further rotates a first-hand ring 151 in a direction of arrow D (clockwise direction when viewed in FIG. 12), the first coupling portion 1135 connected to the first-hand ring 151 may also be rotated further. However, in this state, even if the user presses the first-hand ring 151 in the opposite direction of the arrow D direction (counter-clockwise direction when viewed in FIG. 12), the first coupling Portion 1135 may not rotate in the opposite direction of arrow D because of an interaction of the second coupling portion 171*b* and the first coupling portion 1135. In other words, in a state in which the second coupling portion 171*b* and the first coupling portion 1135 are coupled to each other, it may be said that manipulation is possible only in a direction in which two jaws of an end tool approach each other.

However, in a state in which the second coupling portion 171*b* and the first coupling portion 1135 are not coupled to each other as illustrated in FIGS. 9 to 10, the first coupling portion 1135 is freely rotatable in the clockwise direction or the counterclockwise direction.

The locking portion 171 may be formed such that a region adjacent to the contact portion 171*a* protrudes to an outside of the first handle 114 while most of the locking portion is accommodated inside the first handle 114 so that the user may press the contact portion 171*a* with a finger.

Meanwhile, a first elastic member 173 may be further formed between the locking portion 171 and an inner wall of the first handle 114. The first clastic member 173 may be formed of a compression spring, and may apply a predetermined elastic force so that the locking portion 171 rotates in an arrow A direction (clockwise direction). Therefore, if there is no intervention of a locking control portion 175 to be described later, it may be basically explained that the locking portion 171 is receiving a force in a direction away from the first coupling portion 1135 of the actuation manipulation portion 113. That is, it may be seen that the locking portion 171 is receiving a force to be basically unlocked by the first elastic member 173.

A locking control portion 175 may include a body portion 176 and a pressing portion 177.

The body portion 176 is formed such that at least a portion of the body portion is accommodated inside the first handle 114. Here, the body portion 176 may be fixedly coupled to the inside of the first handle 114.

The pressing portion 177 may be formed to be drawn in and drawn out from the body portion 176. At this time, the pressing portion 177 may be formed to be fixed in a first position (sec FIGS. 9 and 10) when the pressing portion 177 is pressed once, and the pressing portion 177 may be formed to be fixed in a second position (see FIGS. 11 and 12) when the pressing portion 177 is pressed once again. That is, whenever the pressing portion 177 is pressed once, it may be formed to be alternately positioned in the first position and the second position.

Here, as an example of a drawing in/drawing out mechanism of the pressing portion 177 with respect to the body portion 176, an operation mechanism of a tick-tick ballpoint pen may be applied.

Referring to FIGS. 13 and 14, a stop member 176*a* may be fixedly coupled to the inside of the body portion 176. And, a plunger 176*b* may be formed so as to reciprocate in a straight line within the body portion 176. Meanwhile, a cam body 177*a* may be formed in the pressing portion 177. Conversely, the plunger may be formed on the pressing portion 177, and the cam body may be formed on the body portion 176. In addition, although not illustrated in the drawings, a second elastic member (not illustrated) may be additionally arranged between the body portion 176 and the pressing portion 177 to apply an elastic force to the pressing portion 177.

When the user presses the contact portion 171*a* and the pressing portion 177 in contact therewith once, the locking control portion 175 is brought to a state as illustrated in FIGS. 9 and 13 so that the pressing portion 177 may be fixed in the first position, and when the user presses the contact portion 171*a* and the pressing portion 177 in contact therewith once again, the locking control portion 175 is brought to a state as illustrated in FIGS. 11 and 14, so that the pressing portion 177 may be fixed in the second position.

To explain this from another perspective, when the user presses the contact portion 171*a* and the pressing portion 177 in contact therewith once in the state illustrated in FIG. 9, the pressing portion 177 of the locking control portion 175 is drawn out from a body 176 to a certain extent in an arrow B direction as illustrated in FIG. 11. The drawn pressing portion 177 pushes the contact portion 171*a* of the locking portion 171 so that the locking portion 171 as a whole rotates in an arrow C direction (i.e., counterclockwise direction). Then, the second coupling portion 171*b* of the locking portion 171 is also rotated in the counterclockwise direction to be inserted into the first coupling portion 1135 of the actuation manipulation portion 113. Then, the actuation manipulation portion 113 is locked in that state and its movement is restricted.

Next, when the user presses the contact portion 171*a* and the pressing portion 177 in contact therewith once again in the state illustrated in FIG. 11, the pressing portion 177 of the locking control portion 175 is drawn in toward the body 176 to a certain degree in the opposite direction of the arrow B direction as illustrated in FIG. 9. When the pressing portion 177 is drawn in, the locking portion 171 as a whole is rotated in the opposite direction of the arrow C direction (i.e., clockwise direction) by the clastic force of the first elastic member 173. Then, the second coupling portion 171*b* of the locking portion 171 is also rotated in the clockwise direction to come out of the first coupling portion 1135 of the actuation manipulation portion 113. Then, the actuation manipulation portion 113 is unlocked in that state and may be rotated freely.

Here, the direction of the force applied to the locking portion 171 by the elastic force of the second elastic member (not illustrated) arranged between the body portion 176 and the pressing portion 177 and the direction of the force applied to the locking portion 171 by the first elastic member 173 arranged between the locking portion 171 and the first handle 114 may be opposite to each other. In addition, the magnitude of the force (or torque) applied to the locking portion 171 by the second elastic member (not illustrated) may be greater than the magnitude of the force (or torque) applied to the locking portion 171 by the first elastic member 173. Therefore, the locking portion 171 is fixed to the second position in a state in which the elastic force of the second elastic member (not shown) applied to the locking portion 171, and the locking portion 171 may be fixed in the first position by the elastic force of the first elastic member 173 in a state in which the elastic force of the second elastic member (not illustrated) does not apply to the locking portion 171.

According to this disclosure, locking and/or unlocking of at least one operation (e.g., actuation operation) is possible, so that the operator's convenience is improved, and the accuracy, reliability and speed of surgery may be improved. In particular, since the first coupling portion 1135 is formed in a gear-shape having a plurality of cog wheels, locking is possible at a plurality of positions, so that the end tool may be locked at an exact position desired by the user. In addition, by forming the second coupling portion 171*b* in a ratchet shape, it is possible to further pressurize the end tool in the tightening direction (i.e., the direction in which the two jaws come closer) even in the locked state, thereby enabling precise operation such as holding a tissue tightly by further pressing the locking portion 171 after the operator lightly grabs and positions the tissue in the body.

(Actuation Motion, Yaw Motion, Pitch Motion)

Actuation motion, yaw motion, and pitch motion in this embodiment will be described as follows.

First, the actuation motion is as follows.

When a user rotates actuation rotating portions 1132a and 1132b using one or both of an index finger inserted into a hand ring 150 connected to a first actuation rotating portion 1132a and a thumb inserted into a hand ring 150 connected to a second actuation rotating portion 1132b, a first actuation pulley 113P1 fixedly coupled to the first actuation rotating portion 1132a and a first actuation gear 1134a are rotated around a first actuation rotation shaft 1131a, and a second actuation pulley 113P2 fixedly coupled to the second actuation rotating portion 1132b and a second actuation gear 1134b are rotated around a second actuation rotation shaft 1131b. At this time, as the first actuation pulley 113P1 and the second actuation pulley 113P2 rotate in opposite directions, a first jaw wire 130J1 having one end fixedly coupled to and wound on the first actuation pulley 113P1 and a second jaw wire 130J2 having one end fixedly coupled to and wound on the second actuation pulley 113P2 also move in opposite directions. And, this rotational force is transmitted to an end tool 120 through a power transmission portion 130, two jaws 121 and 122 of the end tool 120 perform the actuation motion.

Here, the actuation motion refers to an action of opening or closing the jaws 121 and 122 while the two jaws 121 and 122 rotate in opposite directions to each other, as described above. That is, when the actuation rotating portions 1132a and 1132b of an actuation manipulation portion 113 are rotated in a direction closer to each other, a first jaw 121 rotates counterclockwise and a second jaw 122 rotates clockwise to close the end tool 120, but when the actuation rotating portions 1132a and 1132b of the actuation manipulation portion 113 are rotated in a direction away from each other, the first jaw 121 rotates clockwise and the second jaw 122 rotates counterclockwise to open the end tool 120. In this embodiment, for the above-described actuation manipulation, the first actuation rotating portion 1132a and the second actuation rotating portion 1132b were provided to constitute a second handle, and two fingers were gripped to enable manipulation. However, unlike the above, the actuation manipulation portion 113 for actuation manipulation to open and close the two jaws of the end tool 120 with each other may be configured differently so that, for example, two actuation pulleys (first actuation pulley 113P1, second actuation pulley 113P2) operate opposite to each other by one actuation rotating portion.

Next, the yaw motion is as follows.

When the user rotates a first handle 114 around a yaw rotation shaft 1121 while holding the first handle 114, the actuation manipulation portion 113 and a yaw manipulation portion 112 make yaw rotation around the yaw rotation shaft 1121. That is, when the first actuation pulley 113P1 of a first actuation manipulation portion 113a fixedly coupled to the first jaw wire 130J1 rotates around the yaw rotation shaft 1121, the first jaw wire 130J1 wound on a first jaw yaw pulley 112P1 moves. Similarly, when the second actuation pulley 113P2 of a second actuation manipulation portion 113b fixedly coupled to the second jaw wire 130J2 rotates around the yaw rotation shaft 1121, the second jaw wire 130J2 wound around a second jaw yaw pulley 112P2 moves. At this time, the first jaw wire 130J1 connected to the first jaw 121 and the second jaw wire 130J2 connected to the second jaw 122 are wound around the first jaw yaw pulley 112P1 and the second jaw yaw pulley 112P2, so that the first jaw 121 and the second jaw 122 rotate in the same direction during yaw rotation. And, this rotational force is transmitted to the end tool 120 through the power transmission portion 130, the two jaws 121 and 122 of the end tool 120 performs the yaw motion that rotates in the same direction.

At this time, since a yaw frame 1123 connects the first handle 114, yaw rotation shaft 1121, first actuation rotation shaft 1131a and second actuation rotation shaft 1131b, first handle 114, yaw manipulation portion 112 and actuation manipulation portion 113 are rotated together around the yaw rotation shaft 1121.

Next, the pitch motion is as follows.

When the user rotates the first handle 114 around a pitch rotation shaft 1111 while holding the first handle 114, the actuation manipulation portion 113, the yaw manipulation portion 112 and a pitch manipulation portion 111 make pitch rotation around the pitch rotation shaft 1111. That is, when the first actuation pulley 113P1 of the first actuation manipulation portion 113a fixedly coupled to the first jaw wire 130J1 rotates around the pitch rotation shaft 1111, the first jaw wire 130J1 wound on a first jaw pitch pulley-a 111P1a and a first jaw pitch pulley-b 111P1b moves. Similarly, when the second actuation pulley 113P2 of the second actuation manipulation portion 113b fixedly coupled to the second jaw wire 130J2 rotates around the pitch rotation shaft 1111, the second jaw wire 130J2 wound on a second jaw pitch pulley-a 111P2a and a second jaw pitch pulley-b 111P2b moves. At this time, the first jaw wire 130J1 and the second jaw wire 130J2 are wound on a first jaw pitch pulley 111P1a, 111P1b and a second jaw pitch pulley 111P2a, 111P2b, so that, as described through FIG. 5, both strands of the first jaw wire 130J1 move in the same direction, and both strands of the second jaw wire 130J2 move in the same direction, thus the first jaw 121 and second jaw 122 may perform pitch rotation. And, this rotational force is transmitted to the end tool 120 through the power transmission portion 130, so that the two jaws 121 and 122 of the end tool 120 performs a pitch motion.

At this time, when a pitch frame 1113 rotates around the pitch rotation shaft 1111, the yaw frame 1123 connected to the pitch frame 1113, first handle 114, yaw rotation shaft 1121, first actuation rotation shaft 1131a and second actuation rotation shaft 1131b rotate together because the pitch frame 1113 is connected to the yaw frame 1123, and the yaw frame 1123 connects the first handle 114, the yaw rotation shaft 1121, the first actuation rotation shaft 1131a and the second actuation rotation shaft 1131b. That is, when the pitch manipulation portion 111 rotates around the pitch rotation shaft 1111, the actuation manipulation portion 113 and the yaw manipulation portion 112 are rotated together with the pitch manipulation portion 111.

In summary, in a surgical instrument 100 according to an embodiment of the present disclosure, it is characterized that pulleys are formed at each joint point (actuation joint, yaw joint, pitch joint), wire (first jaw wire or second jaw wire) is wound on the pulley, and rotational manipulation of the manipulation portion (actuation rotation, yaw rotation, pitch rotation) causes movement of each wire, as a result, a desired motion of the end tool 120 is induced. Furthermore, auxiliary pulleys may be formed on one side of each pulley, and the wire may not be wound several times on one pulley by these auxiliary pulleys.

Accordingly, as illustrated in FIG. 7 illustrating a first embodiment, the actuation operation, the yaw operation, and the pitch operation may be performed independently of each other.

As described through FIG. 1, the actuation manipulation portion 113, yaw manipulation portion 112, and pitch manipulation portion 111 have their own rotation shafts located at the back of each manipulation portion, so it is configured the same as the joint configuration of the end tool, allowing the user to perform intuitively matching operations.

Especially, in a surgical instrument 100 according to an embodiment of the present disclosure, it is characterized that pulleys are formed at each joint point (actuation joint, yaw joint, pitch joint), wire (first jaw wire or second jaw wire) is wound on the pulley, and rotational manipulation of the manipulation portion (actuation rotation, yaw rotation, pitch rotation) causes movement of each wire, as a result, a desired motion of the end tool 120 is induced. Furthermore, auxiliary pulleys may be formed on one side of each pulley, and the wire may not be wound several times on one pulley by these auxiliary pulleys, so that the wires wound on the pulley do not come into contact with each other, and the path of the wire that goes into the pulley and the wire that comes out is also formed safely, so the safety and efficiency of power transmission of the wire may be improved.

On the other hand, as described above, the yaw manipulation portion 112 and the actuation manipulation portion 113 are formed directly on the first handle 114. Therefore, when the first handle 114 rotates around the pitch rotation shaft 1111, the yaw manipulation portion 112 and the actuation manipulation portion 113 also rotate together with the first handle 114. Due to this, a coordinate system of the yaw manipulation portion 112 and the actuation manipulation portion 113 is not fixed, but continues to change relatively according to the rotation of the first handle 114. That is, in FIG. 2 and the like, the yaw manipulation portion 112 and the actuation manipulation portion 113 are illustrated as being parallel to a Z-axis. However, when the first handle 114 is rotated, the yaw manipulation portion 112 and the actuation manipulation portion 113 are not parallel to the Z-axis. That is, the coordinate system of the yaw manipulation portion 112 and the actuation manipulation portion 113 is changed according to the rotation of the first handle 114. However, in the present specification, for convenience of explanation, if there is no separate explanation, the coordinate system of the yaw manipulation portion 112 and the actuation manipulation portion 113 was described based on a state in which the first handle 114 is positioned vertically with respect to the connection portion 140 as illustrated in FIG. 2.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

The invention claimed is:

1. Surgical instrument comprising:
   an end tool having a first jaw and a second jaw, each formed to be rotatable, wherein the rotation is made in two or more directions;
   a manipulation portion configured to control rotation of the end tool in the two or more directions;
   a power transmission portion having a first jaw wire connected to the manipulation portion to transfer the rotation of the manipulation portion to the first jaw and a second jaw wire connected to the manipulation portion to transfer the rotation of the manipulation portion to the second jaw; and
   a connecting portion extending in a first direction (X-axis) and having one end coupled to the end tool and the other end coupled to the manipulation portion to connect the manipulation portion and the end tool,
   wherein the manipulation portion comprises
   an actuation manipulation portion configured to control actuation movement of the end tool, and
   a locking device formed to be able to be in contact with the actuation manipulation portion and locking and unlocking actuation operation of the actuation manipulation portion depending on whether the locking device is in contact with the actuation manipulation portion,
   wherein a first coupling portion is formed in the actuation manipulation portion, and a locking portion formed to be able to be in contact with the first coupling portion is formed in the locking device, and
   wherein the first coupling portion is formed in a gear-shape having one or more cog wheels.

2. The surgical instrument of claim 1, wherein
   when the locking portion is in a first position, the locking portion is formed to engage the first coupling portion to restrict movement of the first coupling portion, and
   when the locking portion is in a second position, the locking portion is formed to be spaced apart from the first coupling portion to a certain extent to enable movement of the first coupling portion.

3. The surgical instrument of claim 2, further comprising
   a locking control portion configured to control a position of the locking portion so that the locking portion maintains either the first position or the second position.

4. The surgical instrument of claim 3, wherein the locking control portion comprises
   a body portion disposed within the manipulation portion, and
   a pressing portion coupled to the body portion and formed to be able to be drawn in and drawn out from the body portion.

5. The surgical instrument of claim 4, wherein
   the pressing portion is drawn in the body portion when the pressing portion is pressed once,
   and the pressing portion is drawn out from the body portion when the pressing portion is pressed once again.

6. The surgical instrument of claim 5, wherein
   the locking portion is positioned in the second position while the pressing portion is drawn in the body portion, when the pressing portion is pressed once,
   and the locking portion is positioned at the first position while the pressing portion is drawn out from the body portion, when the pressing portion is pressed once again.

7. The surgical instrument of claim 4, wherein
   a plunger is disposed on any one of the body portion and the pressing portion, and a cam body is disposed on the other one of the body portion and the pressing portion, so that the position of the pressing portion with respect to the body portion is controlled by the relative positional relationship between the plunger and the cam body.

8. The surgical instrument of claim 7, further comprising a second elastic member configured to provide a predetermined elastic force to at least one of the plunger and the cam body.

9. The surgical instrument of claim 1, wherein the locking device is capable of locking the actuation manipulation portion in one or more locking positions.

10. The surgical instrument of claim 9, wherein each of the one or more cog wheels corresponds to the corresponding one or more locking positions.

11. The surgical instrument of claim 1, wherein one surface of the locking portion and one surface of the first coupling portion are each formed to be inclined at a predetermined angle, so as to function as a ratchet when the locking portion and the first coupling portion are fastened to each other.

12. The surgical instrument of claim 1, wherein the first coupling portion is formed to be rotatable in only one of a clockwise direction and a counterclockwise direction while the locking portion and the first coupling portion are fastened to each other.

13. The surgical instrument of claim 1, wherein the manipulation portion further comprises:
 a first handle;
 a yaw manipulation portion formed to be connected to the first handle and controlling a yaw movement of the end tool; and
 a pitch manipulation portion formed on one side of the yaw manipulation portion and controlling a pitch movement of the end tool,
 wherein the actuation manipulation portion is formed on the other side of the yaw manipulation portion.

14. The surgical instrument of claim 13, wherein a first elastic member is arranged between the locking portion and an inner wall of the first handle to apply a predetermined elastic force to the locking portion.

* * * * *